United States Patent [19]

Zacouto

[11] 4,052,991
[45] Oct. 11, 1977

[54] METHOD OF STIMULATING THE HEART

[76] Inventor: Fred Zacouto, 16 rue de la Convention, Paris 15, France

[21] Appl. No.: 616,881

[22] Filed: Sept. 25, 1975

Related U.S. Application Data

[60] Continuation of Ser. No. 536,602, Dec. 26, 1974, abandoned, which is a division of Ser. No. 126,069, March 19, 1971, Pat. No. 3,857,399.

[51] Int. Cl.² ............................................. A61N 1/36
[52] U.S. Cl. ............................................. 128/419 PG
[58] Field of Search .................. 128/2.06 E, 2.06 R, 128/2.06 P, 419 PG, 419 R, 421, 422, 423

[56] References Cited

U.S. PATENT DOCUMENTS

| 3,352,300 | 11/1967 | Rose | 128/2.06 A |
|---|---|---|---|
| 3,460,542 | 8/1969 | Gemmer | 128/419 PG |
| 3,524,442 | 8/1970 | Horth | 128/2.06 A |
| 3,593,705 | 7/1971 | Thomas et al. | 128/2.06 A |
| 3,672,353 | 6/1972 | Crovella et al. | 128/2.06 A |
| 3,716,059 | 2/1973 | Welborn | 128/419 PG |
| 3,870,050 | 3/1975 | Greatbatch | 128/419 PG |
| 3,952,731 | 4/1976 | Worstencroft | 128/2.06 X |

Primary Examiner—William E. Kamm
Attorney, Agent, or Firm—Brisebois & Kruger

[57] ABSTRACT

Device and method for stimulating the heart. The device comprises means for producing stimulating pulses at regular intervals and means responsive to spontaneous heart signals for controlling the transmission of said pulses to the heart in dependence upon the timing and magnitude of the spontaneous heart signals and/or the average intramyocardial pressure. The method comprises producing stimulating pulses at regular intervals and controlling the transmission of stimulating pulses, in response to spontaneous heart signals, in dependence on the timing and magnitude of the spontaneous heart signals. In the absence of spontaneous heart signals, stimulating pulses are produced at predetermined intervals. When spontaneous heart signals occur, an adjustable waiting period is introduced in which to allow a second spontaneous signal instead of a stimulating pulse. The duration of the waiting period is varied as a function of the interval of time which separates two consecutive spontaneous detected signals (i.e., not separated by any artificially induced heart signal).

10 Claims, 23 Drawing Figures

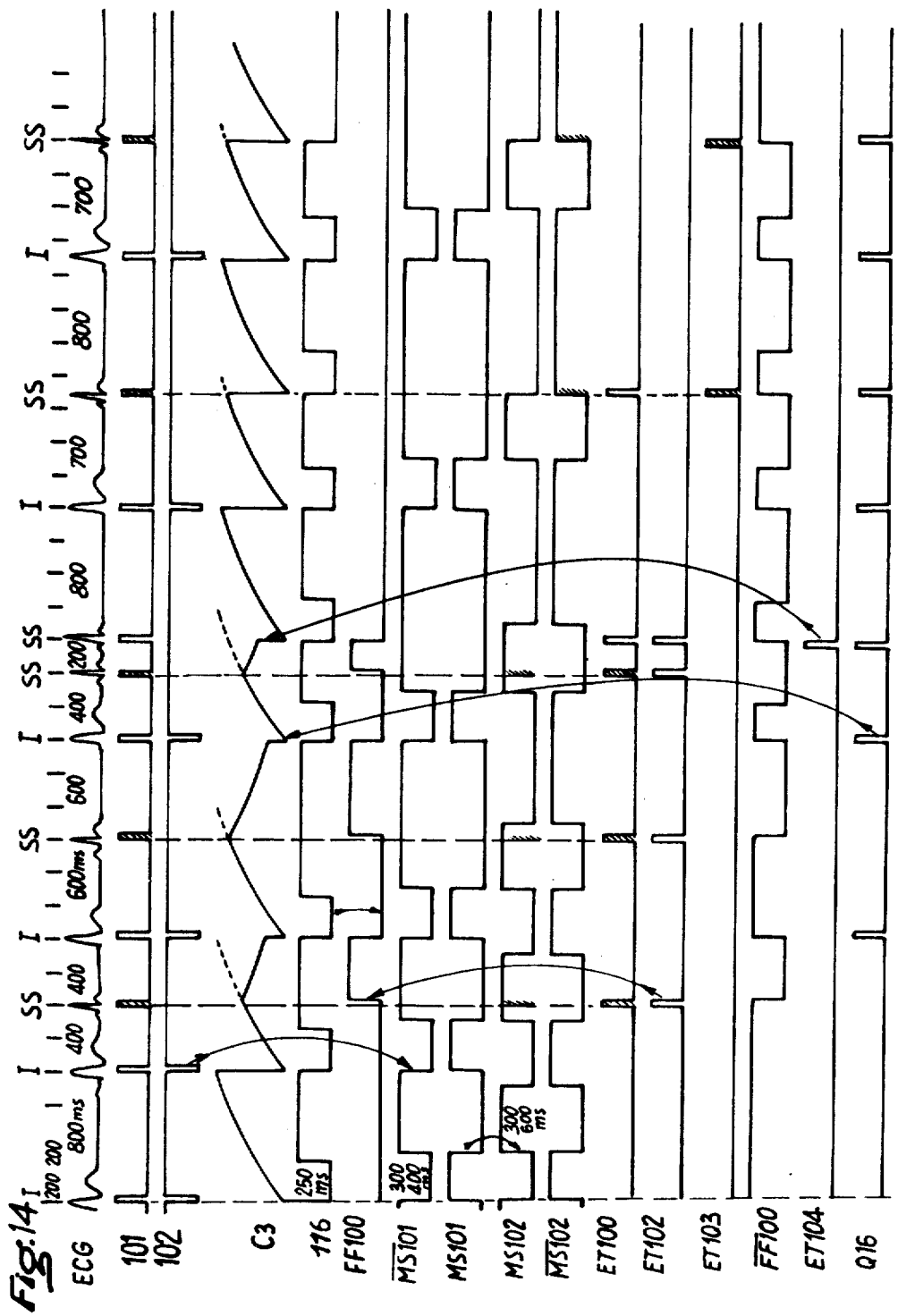

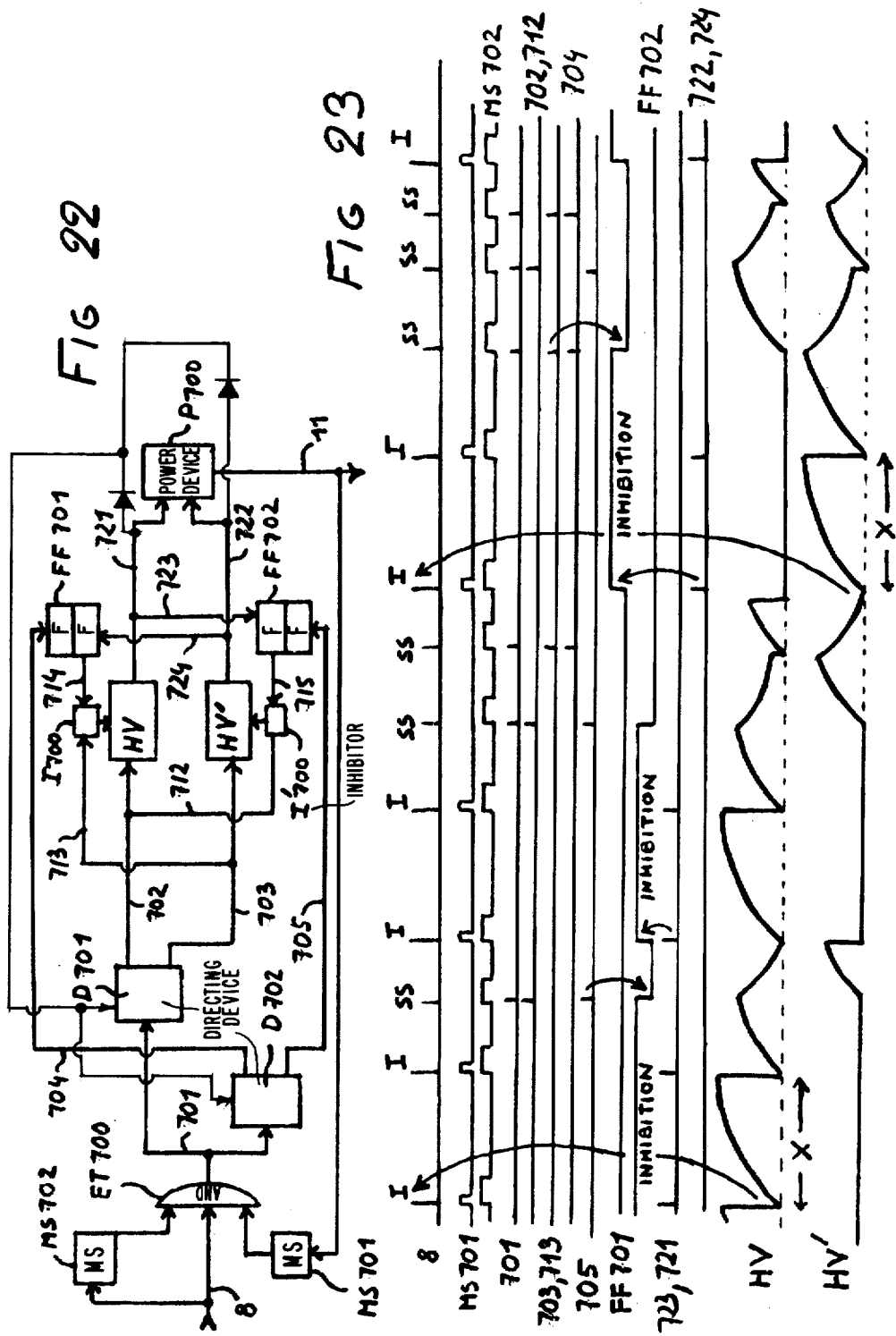

4,052,991

METHOD OF STIMULATING THE HEART

This is a continuation of application Ser. No. 536,602, filed Dec. 26, 1974, (now abandoned), and which was a division of application Ser. No. 126,069, filed Mar. 19, 1971, (now U.S. Pat. No. 3,857,399).

SUMMARY OF THE INVENTION

This invention relates to a method and apparatus for the electrical stimulation of the cardiac muscle.

Known devices for electrically stimulating the cardiac muscle include demand heart pacers which normally stimulate the cardiac muscle at a given frequency by transmitting thereto stimulating impulses at predetermined intervals corresponding to that frequency. When a spontaneous electrical signal called a heart signal from the cardiac muscle occurs which is detected by the electrodes and corresponds, for example, to a cardiac systole, the stimulation is interrupted after this signal for a constant waiting period regardless of whether the spontaneous systole is early or late, and regardless of the nature of this systole. Such devices, while currently in use, have a number of disadvantages. In particular, they offer only an unpersonalized response to the several electrical manifestations which may be produced by the cardiac muscle and may, in certain cases, prevent the heart from returning to beating normally when it indicates a tendency to do so, and, in other cases, permit a dangerous characteristic heart rhythm to be established when it should on the contrary provide corrective intervention.

It is an object of the present invention to provide a process and apparatus making it possible to adapt the artificial electrical stimulation to the instantaneous condition of the cardiac muscle so as to supply a stimulating response which takes into account whether the spontaneous systoles are or are not dangerous.

Another object of the invention is to provide a method and apparatus making it possible to take the cardiac muscle under control when a rapid and dangerous spontaneous rhythm tends to become established.

Another object of the invention is to provide a method and apparatus making it possible to let the heart beat at its own characteristic rhythm when non-dangerous delayed spontaneous systoles occur.

Another object of the invention is to provide a process and apparatus for temporarily increasing the frequency of the stimulation when a dangerous rhythm tends to become established.

Another object of the invention is to provide inexpensive and reliable devices which may be simply adjusted to adapt the responses of the devices very precisely to the instantaneous state of the cardiac patient.

Yet another object of the invention is to provide a device of very simple construction, which is very reliable and consumes very little electrical energy so that it may be implanted in the body.

Other objects and advantages of the invention will appear from reading the following description of the invention, with reference to the accompanying drawings in which:

FIG. 14 is a diagram illustrating the operation of the device shown in FIG. 12;

Figure 16:
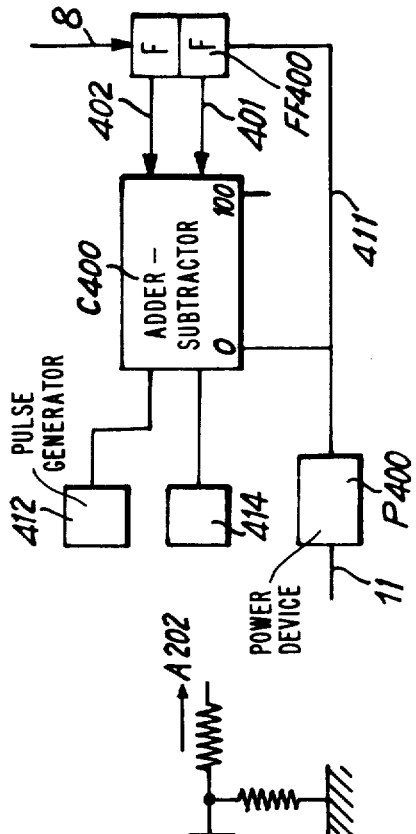
Figure 17:
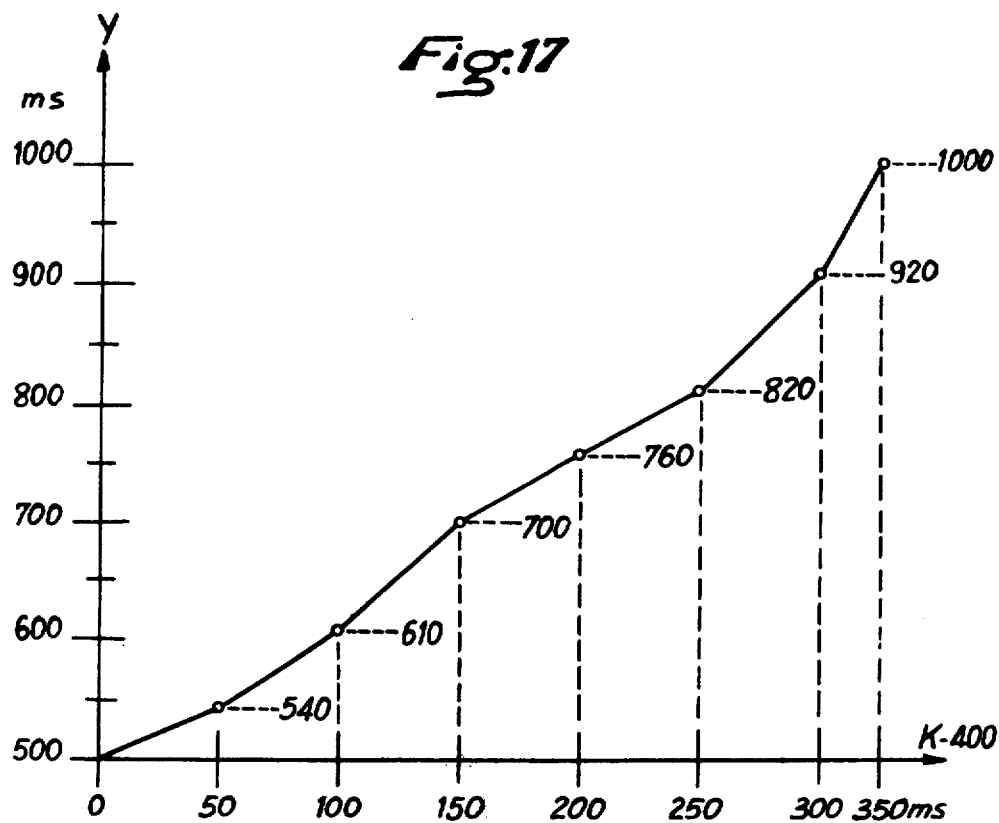
Figure 19:
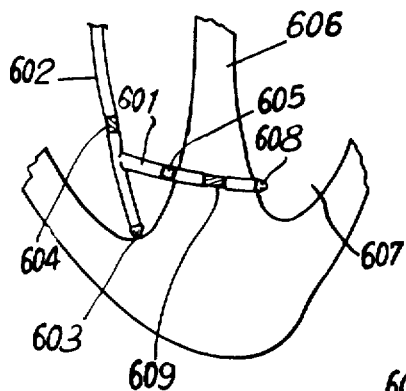
Figure 20:
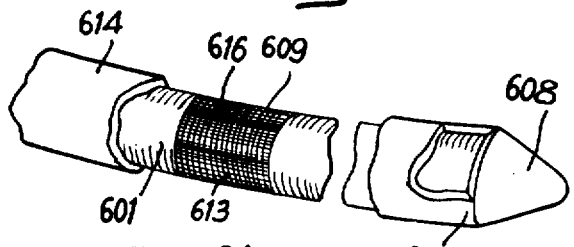
Figure 21:
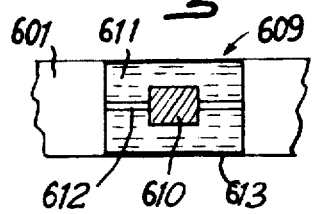
Figure 18:
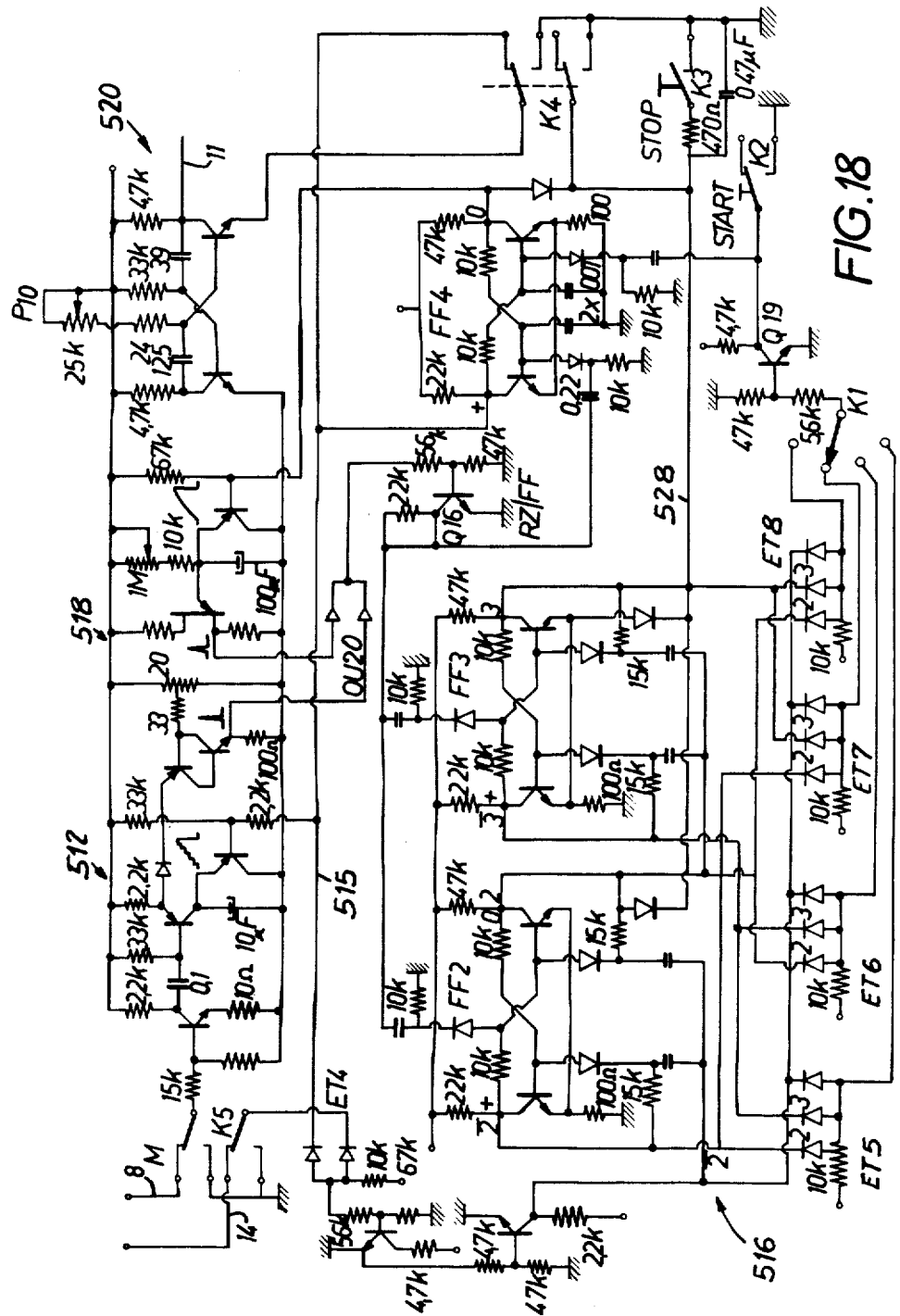

FIG. 16 schematically illustrates yet another embodiment of the part A;

FIG. 17 illustrates an example of the function Y of K;

FIG. 18 is a circuit diagram of the part C;

FIG. 19, 20 and 21 show a device responsive to the intramyocardial pressure;

FIG. 22 is a schematic view of another embodiment of the part A; and

FIG. 23 is a diagram illustrating the operation of the device of FIG. 22.

GENERAL DESCRIPTION OF THE PROCESS

It is the object of the invention to provide a method of electrically stimulating the cardiac muscle by means of an automatic device comprising one or more stimulating and detecting electrodes, in which method electrical stimulating impulses having a predetermined frequency are transmitted to the cardiac muscle in the absence of a spontaneous systole, and the transmission of a stimulating electrical impulse is delayed for a predetermined waiting period when a spontaneous systole of at least a certain type occurs after a stimulating impulse. The waiting period may be of two different durations, at least the shortest of which is less than, or at most equal to, the predetermined period, and the choice of one of the two durations is determined by the interval of time separating the spontaneous systole from the stimulating impulse which directly preceded it. The selected duration of said waiting period is an at least partially increasing function of said interval of time.

Figure 1:
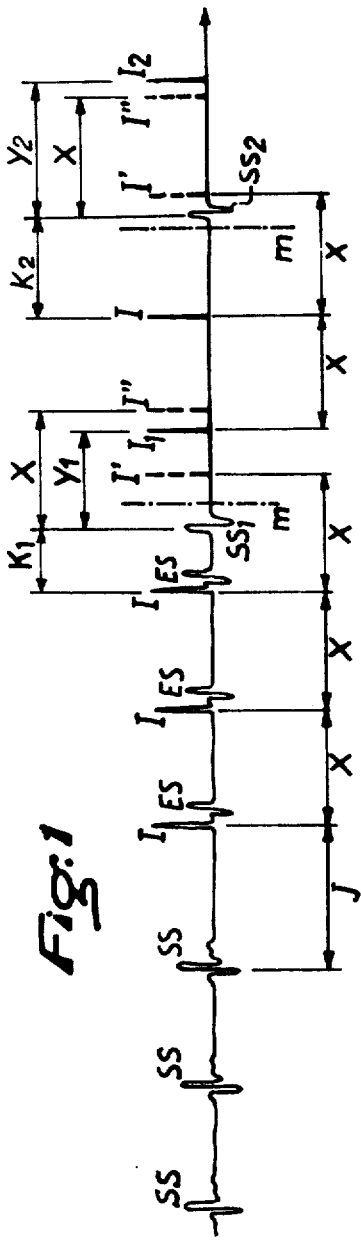
FIG. 1 is a schematic view of an electrocardiogram illustrating the process according to the invention.

FIG. 1 represents an electrocardiogram illustrating the process according to the invention. On this electrical cardiogram three spontaneous systoles SS are shown. After the third spontaneous systole, there is no further spontaneous systole and, in a conventional manner, the device waits a certain period of time J. When no systole occurs during this time, the automatic device, of the demand heart pacer type, transmits a stimulating impulse I which immediately results, at the detection stage, in an electrosystole ES. Since no spontaneous systole appears, there are thus produced, as in a conventional heart pacer, three consecutive stimulating pulses I separated by the time period X which constitutes the predetermined stimulating period in the absence of the appearance of extrasystoles or spontaneous systoles. After the third pulse I, a new spontaneous sysole $SS_1$ is produced, which is separated from the immediately preceding pulse 1 by an interval of time $K_1$. From this moment, in accordance with the invention, a waiting period is permitted to pass which is represented on the drawing by $Y_1$. The drawing also shows at $I'$ the moment at which the next stimulating pulse would have taken place if $SS_1$ had not taken place. If, as shown on the drawing, no new spontaneous systole appears during the period $Y_1$, the apparatus emits a stimulating pulse $I_1$ at the end of this period. Since no new spontaneous systole appears after $I_1$, the device resumes its stimulation at the intervals X by transmitting pulses I as shown on the drawing. If, after such a pulse I, for example the first one on the drawing, a new spontaneous systole $SS_2$ appears, a new waiting period $Y_2$ is initiated and if no spontaneous systole occurs during this time, a stimulating pulse $I_2$ is transmitted to the cardiac muscle at the end of the delay period $Y_2$.

In accordance with the invention, the waiting period Y (such as $Y_1$ or $Y_2$) may have any one of several different values, these values being preferably the smaller as the interval of time, such as $K_1$ or $K_2$ separating the spontaneous systole from the preceding stimulating pulse is the smaller. As shown on the drawing, the value $Y_1$ is smaller than the value $Y_2$ because the period $K_1$ is less than the interval $K_2$. More exactly, it will be seen on the example shown on the drawing that $Y_1$ is less than the period X, and $Y_2$ is greater than the period X. Of course $Y_1$ and $Y_2$ may both be less than the interval X. On the other hand, in accordance with the invention, Y is an increasing function of K, when K increases over a part at least of its range of variation. Nevertheless, in certain particular applications, Y may be a decreasing function of K over a certain part of the range of variation of K.

When, before the end of the waiting period, generally represented by Y, a new spontaneous systole takes place, a new waiting period is established. In a first embodiment, this new waiting period is selected, like the length of the waiting period Y, as a function, this time of the interval of time separating the new spontaneous systole from the preceding spontaneous systole such as $SS_1$ or $SS_2$. In a second embodiment of the invention, this new waiting period is, on the contrary, fixed, and preferably equal to the predetermined stimulating period (X on the drawing). This means that if two directly consecutive spontaneous systoles take place, the second systole is treated as a stimulating pulse and the normal rhythm of stimulation at the predetermined intervals X is resumed.

In one particular embodiment of the invention the different values (such as $Y_1$ and $Y_2$) of the waiting period are discontinuous, the highest values being generally attained for the longest delayed spontaneous systoles and the lowest values for the most premature systoles. Thus, by way of example, if the predetermined interval X is 900 1 milliseconds, the waiting period Y is 600 milliseconds if the interval of duration K separating the spontaneous systole from the immediately preceding stimulating impulse is less than or equal to 500 milliseconds, but equal to 800 milliseconds if K is between 550 and 750 milliseconds, and equal to 1100 milliseconds if K is between 750 and 900 milliseconds. The three different values of the waiting period are thus respectively 600, 800 and 1100 milliseconds. It will be seen that in this particular example the highest value of the waiting period is longer than the interval X. It could, however, be equal to or less than this period. In all cases, as has already been said, the smallest value, at least, of the waiting period, is less than or exactly equal to the duration of the interval X.

However, in a preferred embodiment of the invention, the different values of the waiting period are arranged in a continuous manner and the waiting period is then a continuous, generally increasing, function of the interval of time separating the last pulse from the consecutive spontaneous systole. This function may, however, have steps, especially when the interval approaches the value of said predetermined period X, or on the contrary, when the interval K becomes very small.

Nevertheless, in certain applications, the continuous function Y of X may have a decreasing portion over a certain portion of the range of variation of K.

By way of example, FIG. 17 shows the graphical representation of this function. The ordinate shows the duration Y of the waiting period before stimulation, while the abscissa, decreased by 400 milliseconds, (for reasons of expediency hereinafter explained) shows the interval separating a spontaneous systole from the directly preceding stimulating pulse. The abscissa thus shows the value K-400 milliseconds. This curve may comprise horizontal segments, especially for the highest values of Y, which may, moreover, be greater than the period X.

When the largest values of the waiting period Y are greater than X, that is to say, greater than the period of stimulation in the absence of a spontaneous systole, the value of the interval K beneath which Y is less than X and above which Y is greater than X lies preferably in the second half of the period X which follows the stimulating pulse I directly preceding the spontaneous systole which causes a waiting period. This limiting value is shown at $m$ on FIG. 2. Naturally, if Y is a continuous function of K, Y is equal to X and K is equal to the distance separating I from $m$.

Figure 2:
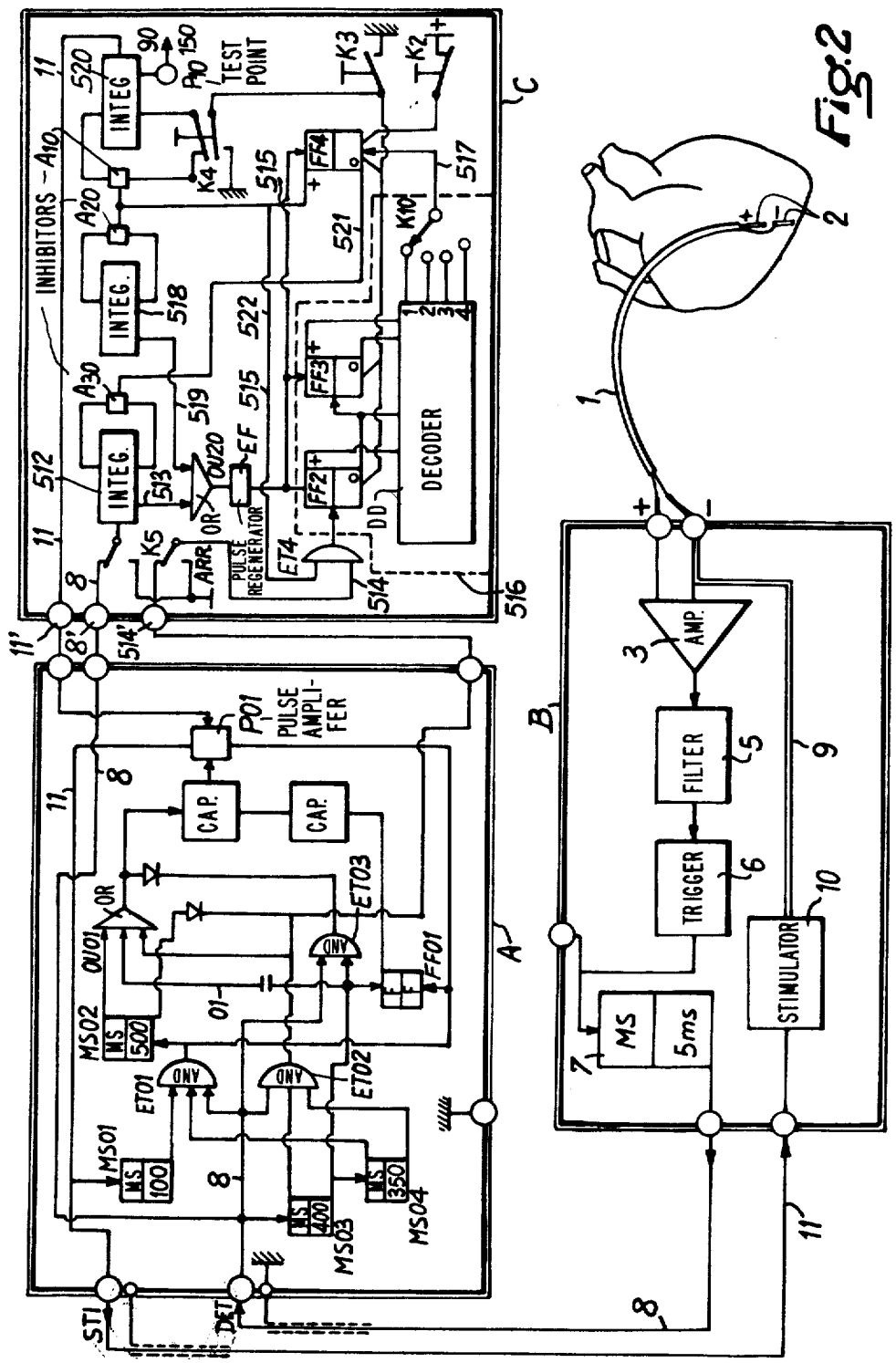
FIG. 2 is a general schematic view of a device according to the invention comprising three parts A, B and C.

In one embodiment of the process according to the invention the waiting period is always greater than the interval separating a spontaneous systole from the immediately preceding stimulating pulse, or, in an alternative form already mentioned, from the immediately preceding spontaneous systole. This means that Y is greater than K. On the contrary, in another form of the invention, Y is always less than K. In this particular embodiment, it is obviously impossible to have in the electrocardiogram three spontaneous systoles SS separated from each other by identical periods of time, as shown at the left of FIG. 2. This alternative has the advantage of insuring energetic taking in hand of the cardiac muscle while leaving it the least possible time within which to produce spontaneous systoles. However, in a third embodiment, Y may be greater than K when K is large and less than K when K is small. It is thus possible to check premature spontaneous systoles while lengthening the waiting period for delayed spontaneous systoles, so as to encourage the cardiac muscle to beat at its own characteristic rhythm, but at a frequency which is not too high.

As has been seen above, the process according to the invention is put in operation when a spontaneous systole of at least a certain type appears. By "systole" is meant any electrical signal of sufficient strength received on at least one of the electrodes, regardless of whether there is or is not a contraction of the cardiac muscle. Thus, in a preferred embodiment of the invention, the process takes into account only those spontaneous systoles which occur after the end of the refractory period of the cardiac muscle, and the systoles which take place during this period are not taken into account. This refractory period is, for a normal cardiac rhythm, for example on the order of 300 to 400 milliseconds after a spontaneous systole or an electro-systole. However, according to the invention, the choice of the type of spontaneous systole which is taken into account may also be a function either of the shape of the systole on the electrocardiogram or of the origin of the spontaneous systole. Thus, the systoles of a certain type may, for example, be limited to ventricular extrasystoles, which are often the most dangerous.

In this case, the detecting electrode may, in accordance with the invention, amount to a waveform discriminator (which will be hereinafter described) or a plurality of electrodes may be used which are located in, or in contact with, the cardiac muscle, the first electrode excited determining the origin of this spontaneous systole.

In accordance with an improved form of the invention, the stimulating pulse normally delivered, or delivered after a waiting period according to the invention, may be at least doubled or its strength may be automatically adjusted, to increase it if a spontaneous systole appears, when the interval of time K is smaller. This assures more certain electrical control of the cardiac muscle, the electrical conductivity of which varies as a function of the instantaneous frequency of the systoles.

In accordance with another improvement of the invention the basic stimulating frequency, that is to say the predetermined period X, is increased in a temporary manner. Y may also be diminished simultaneously to adapt it to this new period X. These alternatives may be selected in dependence on various factors as will be seen from the following.

Thus, if it is found that, despite the variation in the waiting period Y, too large a number of spontaneous systoles are produced, these spontaneous systoles are automatically counted, and when, for a predetermined number of systoles one has counted too large a number of spontaneous systoles, the base period X is automatically decreased.

In another alternative, this base period varies as a function of the intramyocardial pressure detected, as will be hereinafter described. It is also possible to detect by suitable pick-up means the hemodynamic characteristics so as to regulate the rhythm and shape of the stimulating pulses and the waiting periods.

GENERAL DESCRIPTION OF THE APPARATUS

The invention also relates to a device for carrying out the aforesaid process and comprises stimulating means controlled by a time base to deliver at a predetermined frequency electrical pulses for stimulating the cardiac muscle through at least one preferably cardiac electrode, time delay means to control said stimulating means, after a waiting period, by substituting itself temporarily for the time base, said delay means being adapted to be brought into at least two different states for each of which said waiting period has a different length, at least one of the lengths being less than or at most equal to the predetermined waiting period, means for detecting spontaneous cardiac systoles comprising at least one preferably cardiac electrode and for conducting electrical pulses corresponding to the spontaneous systoles detected to said time delay means to initiate said waiting period, which corresponds to the state in which the delay means are found at this instant, and means to shift said time delay means successively from one of said states into the other as a function of the time which has elapsed since the last stimulating pulse.

Said stimulating means may by any conventional means adapted to transmit a stimulating pulse so at least one electrode when actuated by said time base, or by said time delay means, at the end of the waiting period.

The time base may also be of a conventional type. It is thus possible to use as a time base, for example, a capacitance which charges itself periodically through a load resistance and actuates, when charged to a sufficiently high potential, a device such as a programmable unijunction transistor. It is also possible to use an astable switch or multivibrator which periodically initiates the stimulation. It is also possible, as an alternative, to use as a time base a pulse generator operating at a given frequency and associated with any suitable counting means, for example, a flip-flop counter or step-by-step integrator. This counter when the number of predetermined pulses has been counted, causes the emission of a stimulating pulse.

The delay means are responsive to the spontaneous systole pulses coming from the detecting means and may be in either of two different states, so as to initiate the waiting period corresponding to their state at the moment at which they are actuated, and actuate said stimulating means at the end of the said waiting period. It is thus possible to use as delay means two C condenser (i.e. capacitor), each comprising a charging resistor, and both connected to trigger means such, for example, as a programmable unijunction transistor, with one of the condensers charging from an initial potential slightly higher than the initial potential of the other condenser, but increasing in potential more slowly the other condenser, so that the potential of this other condenser in time overtakes the potential of the first condenser, thus actuating a device such as the unijunction transistor. The later the second condenser starts charging after the first condenser has begun to charge, the longer the time which will be required for it to overtake the potential of the first condenser. In this embodiment, the state of the delay means is thus determined by the potential which has been attained by the said first condenser at the moment at which a spontaneous systolic pulse occurs to initiate charging of the second condenser. Of course, instead of using the charging periods of the condensers, it is possible to use their discharge periods.

In another embodiment of the invention, said delay means may consist of a single condenser associated with a discharge resistance. This condenser is charged through a charging resistance which may be the same as the discharge resistance, but which is preferably different. When a spontaneous systolic pulse takes place the charging of the condenser is interrupted and the condenser discharges through the discharge resistance up to the point at which the potential reaches a fixed value from which, through appropriate means, it causes a stimulating pulse to be produced. It will be appreciated that the higher the charging potential is when this pulse takes place, the longer the discharge to the fixed potential constituting the stimulating threshold will take. In this case the state of said time delay means is determined by the potential to which the condenser is charged during the occurrence of a spontaneous systole.

In another embodiment of the invention said time delay means comprise several monostable multivibrators having different periods in the unstable state, at least one of which is less than said predetermined waiting period. These different multivibrators are connected to a electronic actuated rotary switch directing the spontaneous successive systolic pulses as a function of time to the different monostable multivibrators. The state of these time delay means is thus determined by the position of the rotary electronic switch.

In another embodiment of the invention, the delay means comprise a digital pulse counter. Said pulse counter counts a certain number of pulses from a pulse generator and, when it has counted the last of these pulses, actuates the stimulating means. The number of pulses which said counter must count is for example, determined by another number of pulses which has been previously counted, the state of said delay means being thus determined by the number of pulses previously counted and thus by the state of the counter.

This means for changing the state of one of said delay means as a function of the time elapsed since the last stimulating pulse may also be made in various ways. Thus they may comprise a source of potential and a charging resistance associated with a capacitance. The charging of said capacitance starts at the moment at which an electrical stimulating pulse takes place, or, as an alternative, at a predetermined time after such a pulse. The potential attained by said capacitance at the moment at which a spontaneous systole is detected thus determines the state of the associated delay means, for example, a discharge resistance associated with the capacitance.

Thus when the delay means comprises two condensers, the means for changing the delay means from one state to another comprise a source of energy and the charging resistance of the slower condenser. The same is true of the variation utilizing only a single condenser.

In the variation in which said delay means comprises several monostable multivibrators which are made successively responsive, said means for changing the state of one of these delay means comprises means advancing the rotary electronic switch at a predetermined speed from an initial position corresponding to the occurrence of a stimulating pulse. The means for changing the time delay means from one state to another may also comprise digital means including a pulse generator and a counter, for example one which is automatically reset to zero at each stimulating pulse. Beginning when a stimulating electrical pulse takes place, the counter recommences to count the pulses which it receives from the pulse generator. When a spontaneous systole occurs, the state of the time delay means is determined by the number of pulses counted. When the time delay means also comprise a counter, this second counter counts a number of pulses determined by the number of pulses which has previously been counted up to that time by the first counter. The number of pulses counted by the second counter may be, for example, the same as the number previously counted, in which case the waiting period may be equal to or different from the interval of time separating a spontaneous systole from the artificial electrosystole immediately preceding it. Of course, in all embodiments, it is advantageously possible to use common electrical or electronic components, for example for the time base, and/or delay means, and/or means for changing the state of any of the delay means.

The means for detecting spontaneous systoles comprises at least one detecting electrode, which may be the same as the stimulating electrode, and which is adapted to detect cardiac electrical phenomena. Preferably, temporary cut-off means are provided to avoid detection of the cardiac systole directly provoked by an artificial electrostimulation ES. Cut-off means may also be provided to prevent the detection of any cardiac electrical phenomena during a fixed time which follows a stimulating pulse ES, so as to avoid taking into account phenomena which take place during the refractory periods of the cardiac muscle. Finally, said detecting means may comprise different selecting means making it possible to insure the transmission to the delay means of only these pulses received from particular systoles, either as a function of the moment at which such a systole takes place, or as a function of its origin (auricular or ventricular). This is made possible by utilizing two electrodes and determining the position of the electrode which first detected the electrical phenomenon of this systole, or by using means responsive to a characteristic of the electrical systolic pulse, such as its shape, length, amplitude, etc.

The device which has been described may take several forms. It may be that a spontaneous systole detected which has triggered the time delay means will be followed by a second spontaneous systole before the end of the waiting period. In a first embodiment of the invention means are provided to return the different electronic components of the device to their original state so that a second systole is considered by the device exactly like an artificial stimulating pulse.

In another variation of the invention however, means may be provided to again trigger the time delay means to provide a waiting period corresponding to the state in which said time delay means is found at the moment at which the second systole takes place. In this case said time delay means are preferably divided into two parts as will be hereinafter seen.

DETAILED DESCRIPTION OF THE PREFERRED EMBODIMENT

A. FIRST EMBODIMENT

The first embodiment relates to a device comprising two condensers which are charged at two different speeds, the potential of one condenser being adapted to overtake the potential of the other condenser. This device is described with reference to FIGS. 2, 3, 4, 5 and 6.

Referring first to FIG. 2, the device according to the invention comprises three parts A, B and C, of which only parts A and B will now be described. Part C is hereinafter described since it is not indispensable to the operation of parts A and B. Part B comprises an intracardiac catheter 1 which terminates in several electrodes 2, certain of which are positive, while others are negative. These electrodes 2 act both as detectors and as stimulators for the cardiac muscle. The electrodes 2 are connected to an input amplifier 3 of a conventional type which, through a filter 5, leads to a trigger 6 which shapes the pulses detected by the electrodes 2. The trigger 6 leads to a monostable multivibrator MS, the unstable period of which is, for example, 5 milliseconds. The output of MS leads to a detector conductor 8. The part B thus described serves simply to transform the electrical signals received on the electrodes 2 in a conventional manner into signals or pulses calibrated at 5 milliseconds on the conductor 8. The part B also comprises a power conductor 9 for transmitting to the electrodes the stimulating pulses received from a stimulating device 10 of a conventional type controlled through a stimulation conductor 11.

Figure 3:
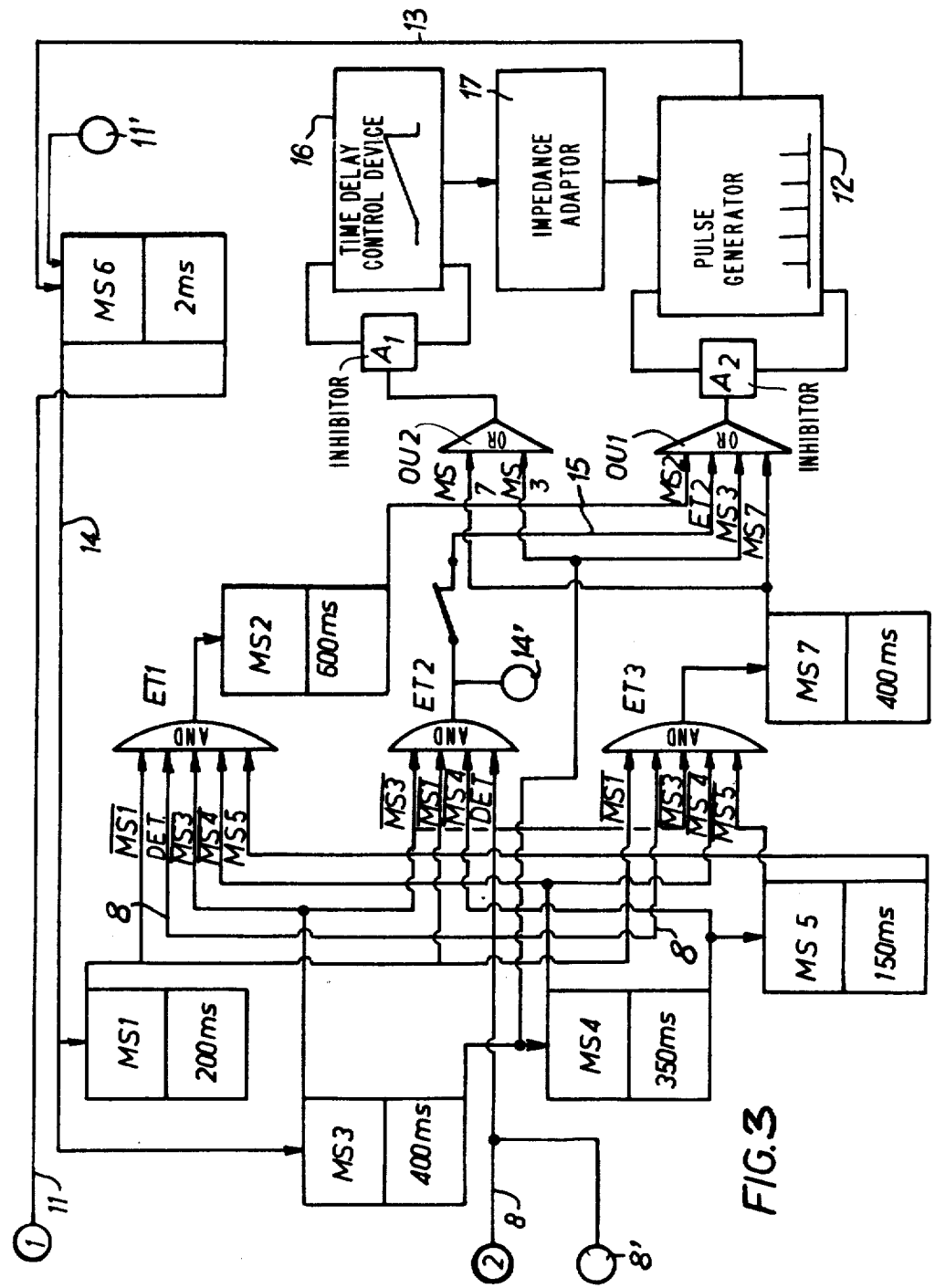
FIG. 3 is an alternative embodiment of the part A.
Figure 4:
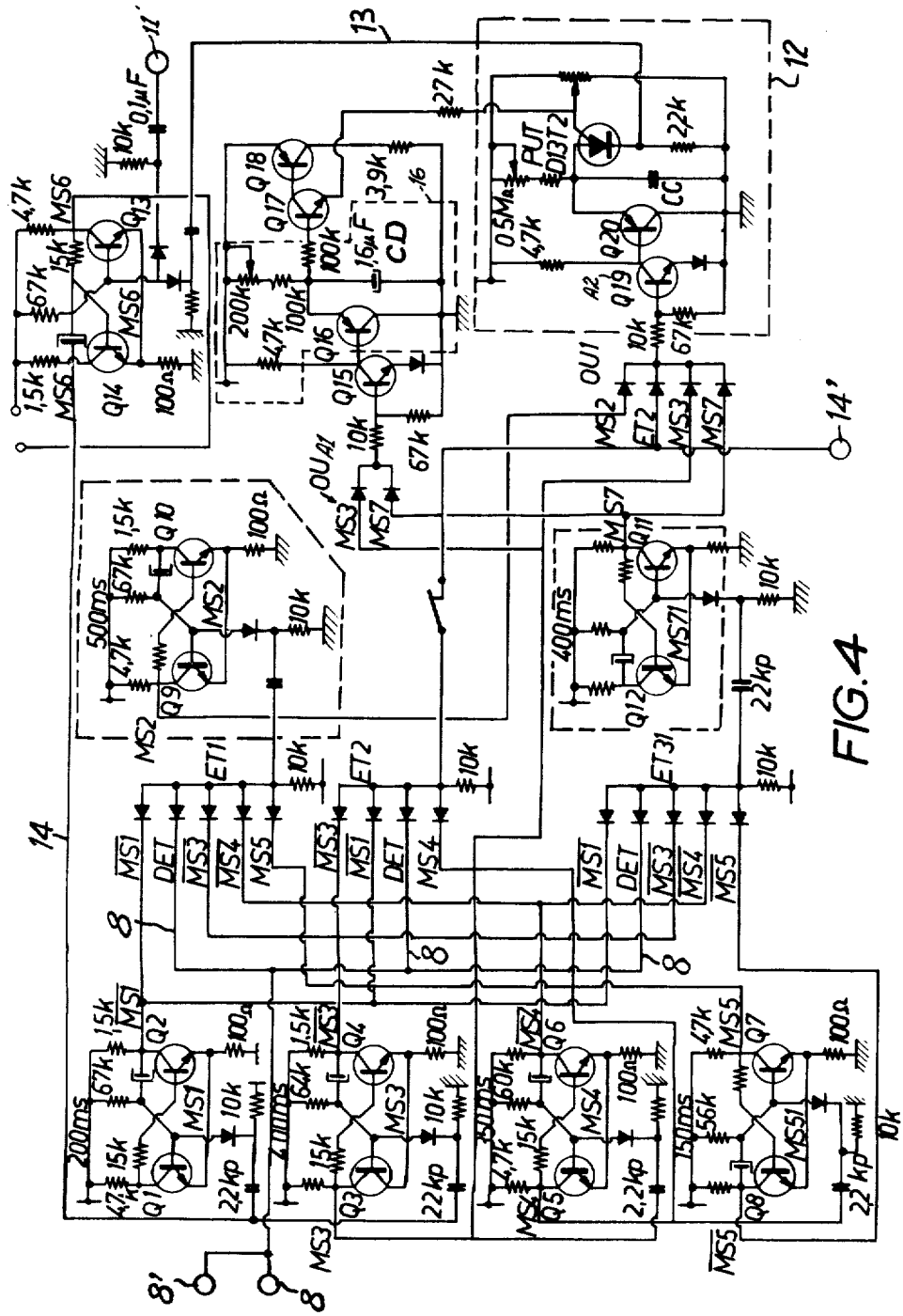
FIG. 4 is a detailed circuit diagram of the apparatus shown in FIG. 3.

Referring now to FIG. 3, on which a variation of the device A is illustrated in detail, it will be seen that the conductors 8 and 11 appear on this Figure. FIG. 4 shows in greater detail the circuitry of the part shown on FIG. 3. As it enters the part A, the conductor 8 leads to a gate ET2, the operation of which will be hereinafter described. The time base comprises a pulse generator 12, the operation of which will be hereinafter described, which is adapted to transmit to an output conductor 13 pulses having normally a predetermined period which is for example 900 milliseconds. This pulse generator comprises, in a conventional manner, a capacitance CC with a charging resistance which is preferably adjustable, for example 0.5 megohms, said capacitance being connected to a programmable unijunction transistor PUT D13T2.

Figure 5:
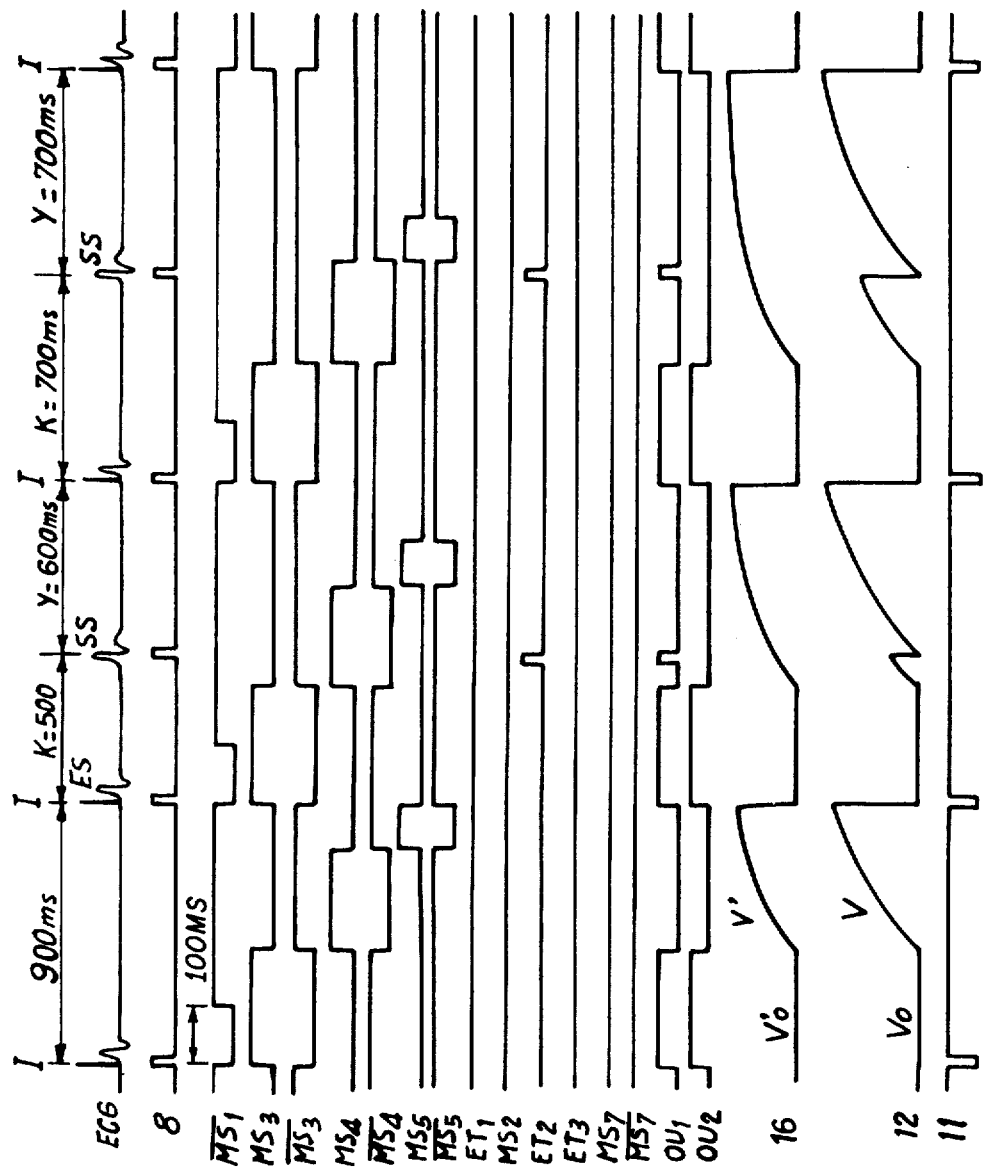
FIGS. 5 and 6 are graphical representations illustrating the operation of the device of FIG. 3.

Consequently, in the absence of a spontaneous systole or spontaneous electrical cardiac signals, the pulse generator or time base 12 insures the operation of the cardiac muscle by emitting each 900 milliseconds a pulse causing the emission by 10 of stimulating pulse I, which is followed immediately by a cardiac electro-systole ES as may be seen on FIG. 5, in which the first line ECG represents the electrocardiogram as it appears at the stage of the electrodes 2. In a more detailed manner, the signal periodically emitted by the time base 12 which is transmitted to the conductor 13 is transmitted thereby to a shaping monostable multivibrator MS6 having a period of 2 milliseconds, an output of which monostable is connected to the conductor 11. Another output 14 from MS6 leads to a monostable MS1 of 200 milliseconds and to a monostable MS3 of 400 milliseconds, respectively. An output from MS3 leads to a monostable MS4 of 350 milliseconds. The output of MS4 leads to a monostable MS5 having a period of 150 milliseconds.

The output of monostable MS1 is connected to three gates, ET1, ET2 and ET3. An output from MS3 is also connected to the gates ET1, ET2, ET3. One output from MS4 is connected to the gates ET1, ET3, whereas the unstable output is connected to ET2. Finally, one output from MS5 is connected to the gate ET3 whereas its unstable output is connected to ET1. Moreover, the detector conductor 8 is also connected to the gates ET1 and ET3.

The gate ET2 is connected by a conductor 15 to a gate OU1, to which the output of MS3 is also connected. The output of gate OU1 is connected to the inhibitor A2 of the pulse generator 12. This inhibiting device comprises the transistor Q19. The output of the gate ET1 is connected to a monostable MS2 having a period of 600 milliseconds, the output of which is also connected to the gate OU1. The output of another monostable MS7 having a period of 400 milliseconds is also connected to this gate OU1 and this monostable is controlled by the output of gate ET3. The output of MS7 is also connected to a gate OU2 to which the output of MS3 is likewise connected. The output of gate OU2 is connected to an inhibiting transistor A1, connected to a time delay control device 16. This device 16 comprises a capacitance CD, for example of 1.6 microfarads, which is charged through a variable resistance for example from 200 to 100 megohms, the potential of this condenser being supplied through an impedance adopter 17, comprising, for example, the transistor Q17, to the gate of the transistor PUT D13T2 of pulse generator 12. In FIG. 4, the adapter 17 and buffers $A_1$ and $A_{12}$ are respctively illustrated as included within the units 16, 12, and 16.

This device operates as follows:

As has been seen, in the absence of a spontaneous systole, the pulse generator 12 stimulates the cardiac muscle at intervals of 900 milliseconds. When the pulse generator 12 transmits a pulse to MS6, this pulse is then directed in the conductors 11 toward the stimulator 10 and also passes through 14 to switch MS1 (having a 200 millisecond period) and MS3 having a 400 millisecond period. In this manner, for 200 milliseconds, as seen labelled on FIG. 5, the unstable output of MS1, that is to say MS1, blocks the gates ET1, ET2 and ET3, and no signal received from the electrodes can pass through these gates. At the end of 200 milliseconds MS1 ceases to inhibit the three gates. However, for 200 milliseconds longer, that is to say up until 400 milliseconds after the pulse I, MS3 inhibits the three gates. During this same period, through the two gates OU1 and OU2, the unstable output of MS3 is supplied to the device A1 and A2, and inhibits the pulse generator 12 and the part 16 of the time delay means. It will be seen, at the beginning of FIG. 5, that the potentials V and V' of the capacitors of 12 and 16 are maintained at their initial value for 400 milliseconds. At the end of these 400 milliseconds, MS3 returns to its stable rest position and, ceases to inhibit the gates ET1, ET2 and ET3 and likewise switch MS4 for 300 milliseconds as seen on FIG. 5. At the same time by ceasing to act on the devices A1 and A2, MS3 permits the output of 12 on the one hand and 16 on the other hand to be distributed.

During the next 350 milliseconds the gate ET2 is not inhibited by MS4 but on the contrary the gates ET1 and ET3 are inhibited by the stable side output of MS4. At the end of these 350 milliseconds MS4 returns to its rest state and then starts MS5 for 150 milliseconds. During these 150 milliseconds, it is ET1 which is open while ET3 is inhibited by MS5. Essentially, the three gates, ET1, ET2 and ET3 function in the following manner. For 400 milliseconds the three gates are blocked, for 350 milliseconds ET2 is open, the two other gates being blocked, and for the last 150 milliseconds, ET1 is open, the two other gates being inhibited.

At the end of 900 milliseconds, (that is to say after charging for 500 milliseconds, since no charge has taken place during the first 400 milliseconds), the potential V' of the condenser CD of the device 16 has been overtaken by the potential V of the condenser C of the time base 12 which started from an initial potential Vo below the initial potential V'o of the capacitance CD of 16, but which increased more rapidly than the potential of CD. At the moment at which the two potentials V and V' become equal, that is to say 500 milliseconds after the start of the charging the transistor PUT D13T2 of the device 12, which is responsive to the equalization of the potentials, emits a pulse through 13 which produces a stimulation I and starting of a new cycle.

(In fact, in practice, the transistor PUT D13T2 is actuated when there is only a slight difference in potential between the charges V and V' on the condensers 12 and 16 independently of the absolute value of the respective potentials of these condensers).

Be it supposed that, in the course of such a predetermined period, a pulse SS from a spontaneous systole occurs. This pulse SS (FIG. 5) suitably shaped by a device B arrives through the conductor 8. If it takes place during the first 400 milliseconds which follow I, the pulse does not pass through any of the gates ET1, ET2 and ET3 and the device continues to operate as hereinbefore described. If, on the other hand, the pulse takes place between 400 and 750 milliseconds, the gate ET2 is open and, passing through 15, the corresponding pulse briefly inhibits the pulse generator 12 through A2, which restarts this generator from its initial potential Vo. It will be appreciated that the later the moment at which the pulse takes place is, the greater the potential V' of the capacitance 16 will be at the moment at which the pulse generator again begins to be charged above its additional potential Vo, and the longer the time the potential V of 12 has to overtake the potential V' of 17. Thus, if the spontaneous systolic pulse takes place just after the first 400 milliseconds, the charges of 12 and 16 start practically at the same time and a stimulating pulse I will then be emitted 500 milliseconds after this spontaneous systolic pulse. If, on the contrary, this spontaneous systolic pulse takes place just before 750 milliseconds, the time which the potential of 12 needs to overtake that of 16 is for example, equal to 700 milliseconds.

Thus, the waiting period Y is longer when the interval separating the spontaneous systole from the last stimulating pulse, that is the delay period K is longer. The 750 millisecond time period has been selected in the preceding Example to define the moment at which it is estimated that a spontaneous systole is no longer dangerous. But of course, this 750 millisecond time period may be decreased or increased in dependence on the needs of the individual patient stimulated, and may well be equal to the predetermined period of 900 milliseconds, in which case it is assumed that all spontaneous systoles taking place after 400 milliseconds are undesirable, but less undesirable the longer they are delayed.

Figure 6:
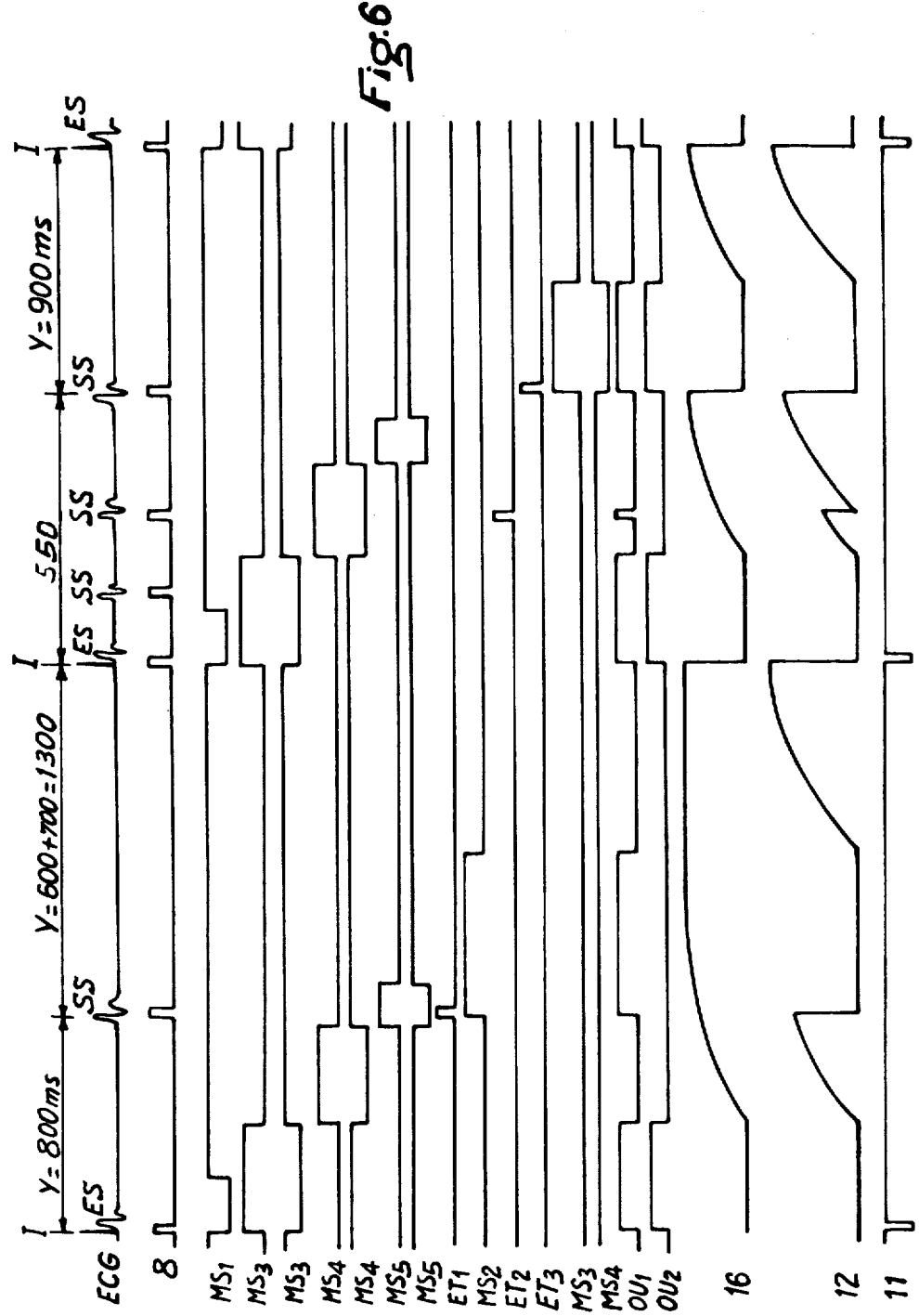

If, now, in the above described device, a spontaneous systole SS takes place not before 750 milliseconds, but after 750 milliseconds, for example at 800 milliseconds, the gate ET2 is no longer open, but ET1 is now opened for 150 milliseconds by MS5 (FIG. 6). The corresponding pulse which passes through the gate ET1 may then start up the monostable MS2 for 600 milliseconds. During the 600 milliseconds, MS2 in unstable state, maintains the pulse generator 12 cut-off by the gate OU1, so that the condenser 12 does not charge. At the end of these 600 milliseconds, MS2 returns to its stable position and the pulse generator 12 then starts up so that the potential V of its capacitance overtakes the charging potential V' of 16, which last potential V' has had time to attain its maximum value V'1 and to maintain that value for 600 milliseconds. Under these conditions, the delay Y is equal to 600 milliseconds plus the time required by V to reach the value V'1. This time is, for example, equal to 700 milliseconds. The waiting period Y will thus be 1300 milliseconds from the time of the spontaneous systole.

It is obvious that this is true regardless of the time at which the pulse SS takes place after 750 milliseconds. It will be ssen that, in this embodiment, for the delayed spontaneous systole, Y is greater than the predetermined period of 900 milliseconds.

A stimulating pulse I having been transmitted over the conductor 11, it will now be supposed that a spontaneous cardiac systole is detected after a time K between 400 and 750 milliseconds, for example for 550 milliseconds (FIG. 6), that is to say while MS4 is unstable and ET2 is open. As has been previously seen, this pulse brings the capacitance CC of 12 to its starting potential Vo. It starts up quickly and engenders the variable delay period Y. If, before the end of this waiting period Y, a new spontaneous systolic pulse takes place, three situations are possible: In the first case, MS4 is still in its unstable state. This case (not illustrated on the drawings,) is extremely rare because this would mean that the two spontaneous systoles were separated by less than 350 milliseconds. In this case, the pulse simply passes again through ET2 and again resets to its starting potential Vo the capacitance CC of 12 which quickly recharges, engendering a new waiting period Y, this time longer.

In the second case (not illustrated), MS4 is returned to its rest position but MS5 is switched. The same thing happens as in the case of a delayed systole (previously described), that is to say, a waiting period of 1300 milliseconds starts.

In the third case illustrated on FIG. 6, MS5 has already returned to its stable position and none of the monostables MS1, MS3, MS4 and MS5 is unstable. Under these conditions, it is the gate ET3 which is open and the spontaneous systolic pulse SS swings MS7 to its unstable state for 400 milliseconds and MS7 for these 400 milliseconds, through the inhibitors A1 and A2, maintains the device 12 and 16 at their initial potential. After 400 milliseconds, 12 and 16 start up at the same time and operate for 500 milliseconds so that V overtakes V' in potential, and then delivers a stimulating pulse after a delay which follows by 900 milliseconds the occurrence of this second spontaneous systolic pulse.

If a third spontaneous systolic pulse takes place after the end of this waiting period of 900 milliseconds, nothing happens if less than 400 milliseconds has passed since the second spontaneous systole that is to say if MS7 is unstable, whereas if this third spontaneous systole takes place after 400 milliseconds it restarts MS7 through ET3 for 400 milliseconds and a new waiting period equal to the predetermined waiting period is set up. Under these conditions, if tachycardia appears, the device according to the invention does not intervene.

In conclusion, the apparatus of FIG. 3 makes it possible to adjust the time delay Y in dependence upon the duration of the period K when a spontaneous systole is detected and selected after an electrical stimulating pulse delivered by the apparatus. If, on the contrary, there is a second spontaneous systole following directly a first spontaneous systole, the device does not intervene to interrupt a tachycardial rhythm.

Another variation of the apparatus A will now be described, again with reference to FIG. 2.

In this variation, the detector conductor 8 also leads to the three gates ET01, ET02, ET03. These gates are opened in the following manner: After a stimulating pulse I, or after a detected systole SS, the gate ET02 is blocked for 400 milliseconds, the others being open during this time (except for ET01 which must be blocked for the first 100 milliseconds by MS01 after a stimulation I). After 400 milliseconds MS03 switches into its stable position, ET02 is opened by MS04, and ET01 and ET03 are blocked for 350 milliseconds. After these 350 milliseconds, ET02 is again closed and ET01 and ET03 are opened.

In this embodiment, MS03 has an output leading to a flip-flop FF01 which may be switched through the conductor 11 (from PO1) to inhibit and maintain discharged the capacitance of a device 016 analogous to the device 16 previously discussed.

When, after the first 400 milliseconds, MS03 returns to its stable position, switching MS04, it will be seen that MS03 switches flip-flop FF01 and this permits the charging of the capacitance 016.

At the end of a certain period of time, for example 500 milliseconds, in the example selected, the potential of 012 exceeds the potential of 016. It is to be noted that in this case 012 begins charging until an impulse I takes place. But at the moment at which MS03, after 400 milliseconds, returns to its stable position, it discharges the capacitance of 012 through a conductor 01 and the gate OU01. Thus, after 400 milliseconds, the charging of 012 and 016 starts at the same time and equality in the potentials is obtained 500 milliseconds after the stimulation has taken place.

If, after 400 milliseconds and before 750 milliseconds, a spontaneous systole SS occurs, it passes through the gate ET02, the output of which is connected to the gate OU01, which again rapidly discharges the capacitance of 012, the potential of which thus falls below that of 016, and the waiting period Y is thus created.

If, on the contrary, the systole SS takes place after 750 milliseconds, it is the gate ET01 which is opened and the pulse from the output of this gate reaches a monostable MS02 having a period of 500 milliseconds (the durations of the unstable periods of the monostables being indicated on FIG. 2) which, after a delay of 500 milliseconds, discharges the capacitance of 012 which then begins to overtake that of 016 and a waiting period Y greater than 1100 milliseconds results.

If the systole takes place during the first 400 milliseconds, the gate ET03 is open and the pulse then simply resets the time base 012 to zero, that is to say, it discharges the capacitance 012.

SECOND PREFERRED EMBODIMENT OF THE INVENTION

In this second embodiment of the invention the time delay means comprise a capacitance having a discharge resistance and when the discharge voltage reaches a small predetermined value, said time delay means initiate the stimulation.

Figure 8:
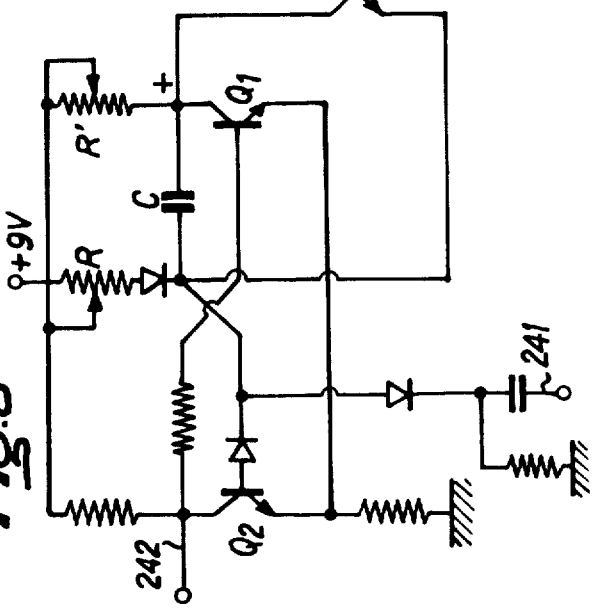
FIG. 8 is a circuit diagram of the delay means of FIG. 7.
Figure 7:
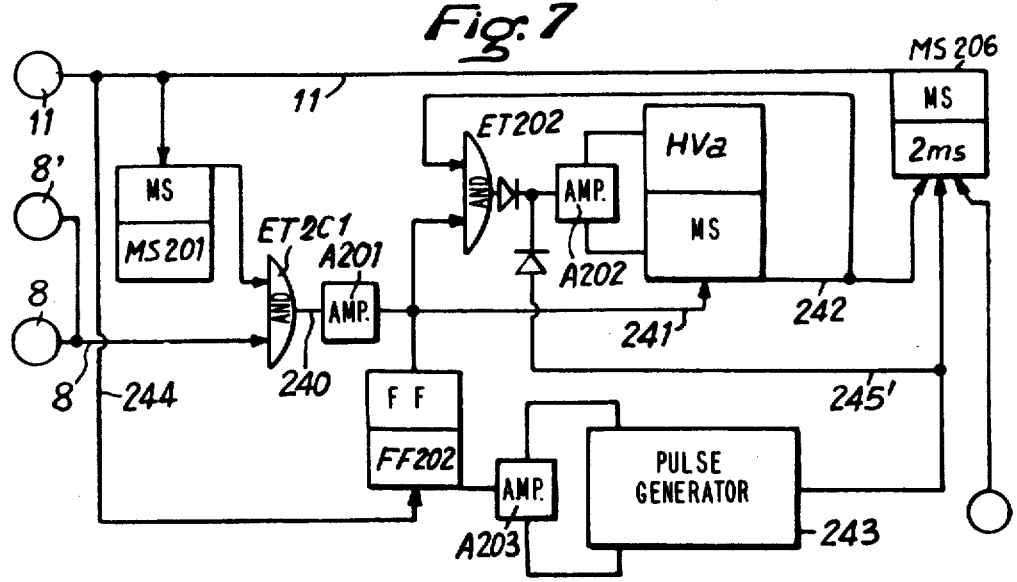
FIG. 7 shows another embodiment of the part A.
Figure 9:
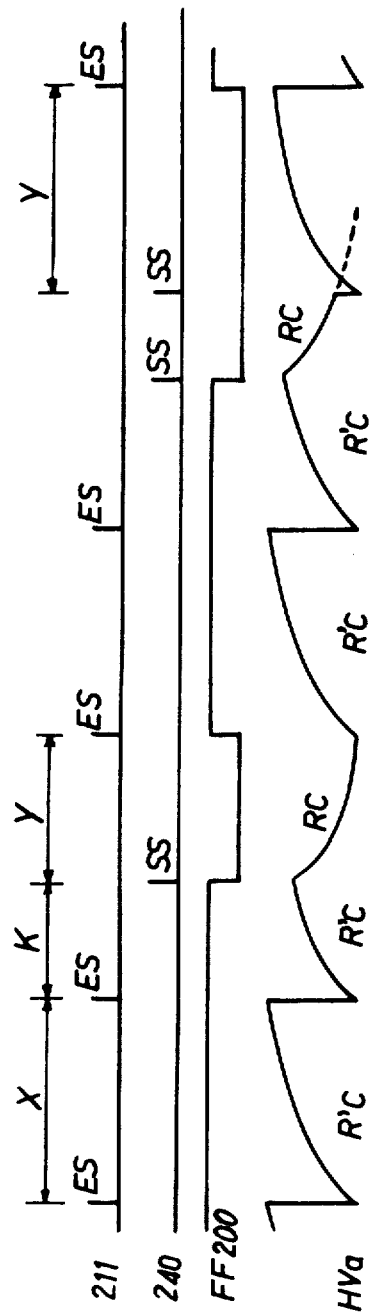
FIG. 9 is a diagramatic representation illustrating the operation of FIG. 7.

Three variations of this second embodiment of the invention will be described. The first variation is illustrated by FIGS. 7, 8 and 9. In the first of these three variations a new apparatus replaces the device A hereinbefore described. In this new device according to FIG. 7 a detector conductor 8 has a branch which crosses the device to reach at 8' the input of C. The stimulating output 11 leads to a monostable MS206 having a reset period of 2 milliseconds. The stimulating output 11 has a branch leading to another monostable MS201, for example of 200 milliseconds, which is adapted to block, after emission of an artificial stimulation along 11, a gate ET201 during a delay period, for example, of 200 milliseconds. The second input of the gate ET201 is connected to the conductor 8 of the systole detector. The output 240 of the gate ET201 is connected through a buffer transistor A 201 on the one hand to one input of a gate ET202 and on the other hand to an input of a flip-flop FF202, and finally to an input 241 of a monostable HVa normally inhibited by a transistor A202 mounted at the output of the gate ET202. The construction of HVa is shown in detail on FIG. 8, said monostable being characterized by a charging resistance R' which is large in proportion to that of conventional monostables. The output 242 of this monostable comprises a branch leading to the second input of the gate ET202. This output leads also to the shaping monostable MS206.

An output of the flip-flop FF202 also leads to a transistor A203 adapted to inhibit a pulse generator 243 connected to transmit pulses to MS206 and thus stimulate the cardiac muscle. A lead 244' from the conductor 11 leads to the other input of the flip-flop.

The operation is as follows: In the absence of a spontaneous systole the pulse generator, which may be of a conventional type, for example an integrator, which periodically transmits a stimulating pulse to MS206, and thence to the conductor 11, emits an artificial stimulating pulse I at the predetermined stimulating interval. This pulse is transmitted, on the one hand, to the electrodes 2 and on the other hand to MS201, which blocks the gate ET201 for 200 milliseconds to prevent the detection of the systole provoked by this stimulation. Finally, this impulse arrives through 244' at the flip-flop FF202 but the latter has already been switched to permit the operation of the pulse generator, so that it does not change its position. Simultaneously, the output pulse of the pulse generator 243 reaches through conductor 245' the output of the gate ET202 so that by acting on the inhibiting transistor A202, HVa, which had begun to be charged by the circuit R'C, is abruptly discharged, without which HVa would acquire a blocking charge during the operation of the pulse generator 243. It follows that at the output 242 of HVa a pulse is directed to the stimulation like 11 but which, since it occurs immediately after the pulse of the pulse generator 243, falls during the wave QRS of the systole provoked by the pulse generator, so that it has no effect on the cardiac muscle. In this manner, in the absence of a spontaneous systole, it is the pulse generator 243 which dictates the cardiac rhythm.

If a spontaneous systole now takes place, more than 200 milliseconds after the last artificial electrical stimulation I, the gate ET201 is open so that the pulse passes through the gate and switches FF202 which then inhibits A203 and blocks the pulse generator 243. Simultaneously this pulse passes through 241, which switches HVa into its unstable position and insures the discharge of the capacitance C which discharges this time through the resistance R as a consequence of the arrangement of the transistor in the monostable.

The output 242 is then at a positive potential. When the monostable is discharged, it returns to its stable position emitting a pulse along 242 which, transmitted through MS206, stimulates the heart.

The conductor 244' then switches the flip-flop FF202 into the position in which it again cuts in the pulse generator 243 and, if no other spontaneous systole takes place, the pulse generator insures the stimulation of the heart at its proper rhythm.

The operating diagram of FIG. 9 shows first the artificial electrosystoles ES produced by the pulse generator 243. Between two successive electrosystoles ES, the charging of the capacitance C by the resistance R' is seen, followed by the sudden discharge which takes place at the moment of the next electrosystole. When a spontaneous systole SS takes place, the flip-flop FF202 is swung and stops 243. At the same time the capacitance discharges through the resistance R and its discharge moment is longer to the extent that the charging time width has been longer. The next artificial stimulation takes place after a waiting period which is variable in dependence upon the period separating the spontaneous systole and the electrosystole which immediately preceded it. In a general way, the time constants are so selected that the time Y separating a spontaneous systole from a stimulating electrosystole which normally follows it is longer than the time K which separates the spontaneous systole from the electrosystole which immediately preceded it, which permits the cardiac muscle to return to a spontaneous rhythm. However, it would be possible to select this time shorter so that the stimulating device would still have a tendency to take the cardiac muscle in hand upon the apparition of a spontaneous systole.

It will also be seen, toward the right of FIG. 9 that if a second spontaneous systole SS takes place after a first spontaneous systole, before the capacitor C has fully discharged, ET202 is then opened and the systole is directed to A202 to suddenly discharge the capacitor which immediately begins to recharge itself.

The device is thus always ready to operate, regardless of whether the spontaneous systole takes place after an artificial systole, or takes place after a spontaneous systole. In this case of tachycardia, the device no longer stimulates.

Depending on the conformation of the charging and discharging curves, it is possible, in a first variation, to have a discharge resistance R such that, regardless of the moment at which a spontaneous systole takes place after an electrosystole immediately preceding it (and of course before the hypothetical electrosystole which would follow this preceding electrosystole, if the spontaneous systole had not intervened,) the delay Y which separates the spontaneous systole from the following electrosystole, that is to say the delay during a discharge of C (if no subsequent spontaneous systole abruptly stops this discharge) is less than the predetermined period X of pulse generator 243, said smaller delay increasing however with the time which separates the spontaneous systole from the immediately preceding systole. In another embodiment, it is possible to adjust R so that the normal delay represented by the discharge of the capacitance is less than the base period X of the pulse generator 243 when the spontaneous systole occurs after a relatively short delay following the immediately preceding systole, whereas this delay beomes greater than this base rhythm when the spontaneous systole takes place after a longer delay. In other words, in this case, when the capacitance C has very little time to charge, it discharges in a time less than the predetermined period, whereas if it has plenty of time to charge, it discharges in a time longer than X.

Figure 11:
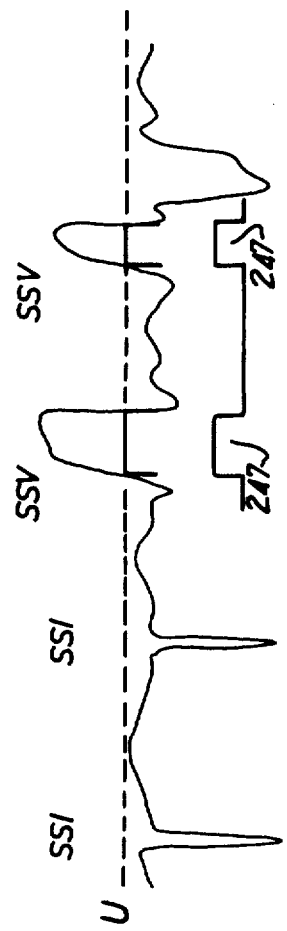
FIG. 11 is a diagram illustrating the operation of FIG. 10.
Figure 10:
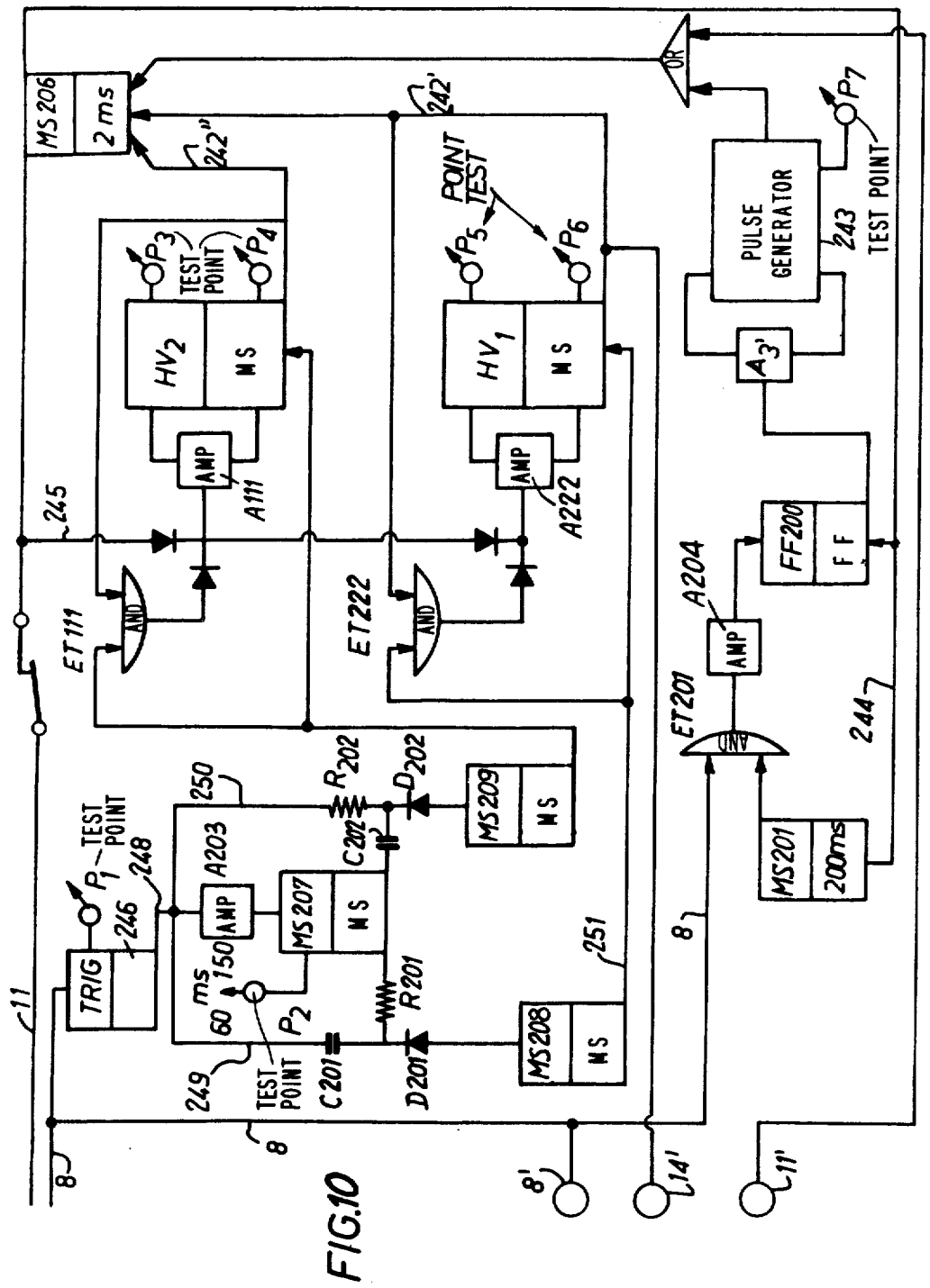
FIG. 10 shows another embodiment of the device of FIG. 7 adapted to detect ventricular systoles.

Referring now to FIGS. 10 and 11, in this second variation, the device shown also comprises a detector conductor 8 leading, as in the case of FIG. 7, to a pulse generator 243 providing a base rhythm, the generator being started or stopped in the same way. However, in the example of FIG. 10, the output of the gate ET201 is not connected to a monostable such as HVa, nor to a gate such as ET202.

Before describing the device of FIG. 10 in greater detail, it will be recalled that among the spontaneous cardiac systoles there are sinusal systoles which are generally not dangerous and ventricular systoles which may be dangerous even if delayed. FIG. 11 illustrates an extremely schematic electrocardiogram showing, on the one hand, sinusal systoles SSI and, on the other hand ventricular systoles SSV, with the second of the two spontaneous ventricular systoles having both a positive and negative peak. Referring again to FIG. 10 it will be seen that the detector conductor 8 comprises a lead connected to a trigger 246 of a known type which, when the potential on 8 exceeds a predetermined value U emits a square wave 247 having a predetermined potential throughout the period during which the potential on 8 is greater than or equal to U. The output 248 of the trigger is connected on the one hand through amplifier A203 to a monostable MS207 (see FIG. 10) the unstable state of which may be adjusted to last for from 60 to 150 milliseconds for example, by a suitable potentiometer. The output 248 is, on the other hand, connected by a conductor 249 to a first discriminator comprising a capacitance C201, a negatively biassed diode D201, and a resistor R201 connecting the common terminal of the capacitance and diode to the output of MS207. A second conductor 250 leads to a second discriminator comprising a resistance R202, a negatively biassed diode D202 and, between the output of MS207 and the common terminal of D202 and R202, a capacitance C202. The diode D201 leads to a monostable MS208, the output 251 of which is connected, on the one hand, to a monostable HV1, of a type similar to HVa, and on the other hand to a gate ET222 through which it is possible to abruptly discharge HV1 by means of an inhibiting transistor A222. A conductor 245 is connected to the output of ET222 and to the stimulating conductor 11 on the other hand. The second input of the gate ET222 is connected to a line from the output 242' of HV1 leading to MS206. In the same manner, the output of MS209 is connected to HV2 through ET111, the arrangement being exactly the same as for HV1, with HV2 connected to MS206 by 242".

The operation of the pulse generator 243 is identical to that of FIG. 7 when a systole detected by 8 takes place. The corresponding pulse is transformed by the trigger 246 into a square wave, the period of which corresponds to the length of the systole. From the beginning of the signal emitted by the trigger 246, the monostable MS207 is astable for a predetermined period, for example, 90 milliseconds, rendering positive its output on R201 and C202 which are normally at zero potential. Two cases will now be considered, dependent on whether MS207 returns to its stable state before the signal from the trigger 246 ceases, or whether MS207 regains its stable state after the end of this square wave signal of the trigger. In the first case, it is presumed that an extra-ventricular systole has occurred. In this case the negative trailing edge of the trigger signal, that is to say the end of the square wave signal, reaches C201 at the moment at which MS207 has returned to its initial position, and the potential of R201 is zero. The negative trailing edge may then pass through the diode D201 and switch the regenerating monostable MS208, the unstable state of which lasts for example from 2 to 5 milliseconds, and which then transmits a signal to 251 which, as in the case of FIG. 7, places HV1 in its unstable position and discharges HV1. At the end of the discharge, the duration of which is longer when the extra systole has been later, that is to say when the capacitance has had more time to charge, HV1 transmits a stimulation through MS206 and the conductor 11. While HV1 is in its unstable position the gate ET222 is open and if a second ventricular extra-systole passes through MS208 it will return HV1 abruptly to zero, as in the case of FIG. 10. The conductor 245 makes it possible, when any stimulation is transmitted over 211, to reduce the capacity of HV1 to avoid its acquisition of a blocking charge.

If, on the contrary, the end of the trigger signal has taken place before the return of MS207 to its stable state, the potential of R201 is positive, greater than the negative trailing edge of the wave from the trigger and the latter cannot pass through the diode D201. On the contrary, the negative trailing edge of the end of the signal MS207 is directed to the capacitance C202 and this negative signal may then pass through the diode D202 since the potential of the common terminal of R202, C202 and D202 has again become zero during the end of the trigger signal 246. In this case it is MS209 which is switched and acts in the same manner as before on HV2 which, at the end of a certain time, is stimulated by MS206. It will be appreciated that the time constants of HV1 and HV2 are different, the stimulation taking place for example sooner for HV1 and later for HV2. Of course, as in the case of HVa, the resistances R and R' are adjustable by means of potentiometers so that the delay in response can be adjusted, for example, in dependence upon the needs of the particular patient.

Of course, it would be possible to replace the trigger 246 by other means for determining the amplitude of the detected wave QRS and producing a square pulse having substantially the amplitude of this wave QRS. In order to detect the full amplitude of the extra-systoles having a positive peak and a negative peak it is, for example, possible to place in parallel with the trigger 246 a second trigger responsive to a negative potential and delivering a signal at the same polarity, provided that a device permitting the signal of any one of the two triggers to be slightly prolonged is connected to the output of each of the two triggers, so as to supply in any case a continuous square wave signal, even then the cardiac wave passes through an intermediate point of zero potential.

It is also possible, in the device according to FIG. 10, to eliminate the device HV2 and its components if it is felt that, in the case of a sinusal systole, it is unnecessary to have a variable time delay Y. In FIG. 10, points $p_1$ through $p_7$ provide test points for testing the apparatus.

Figure 12:
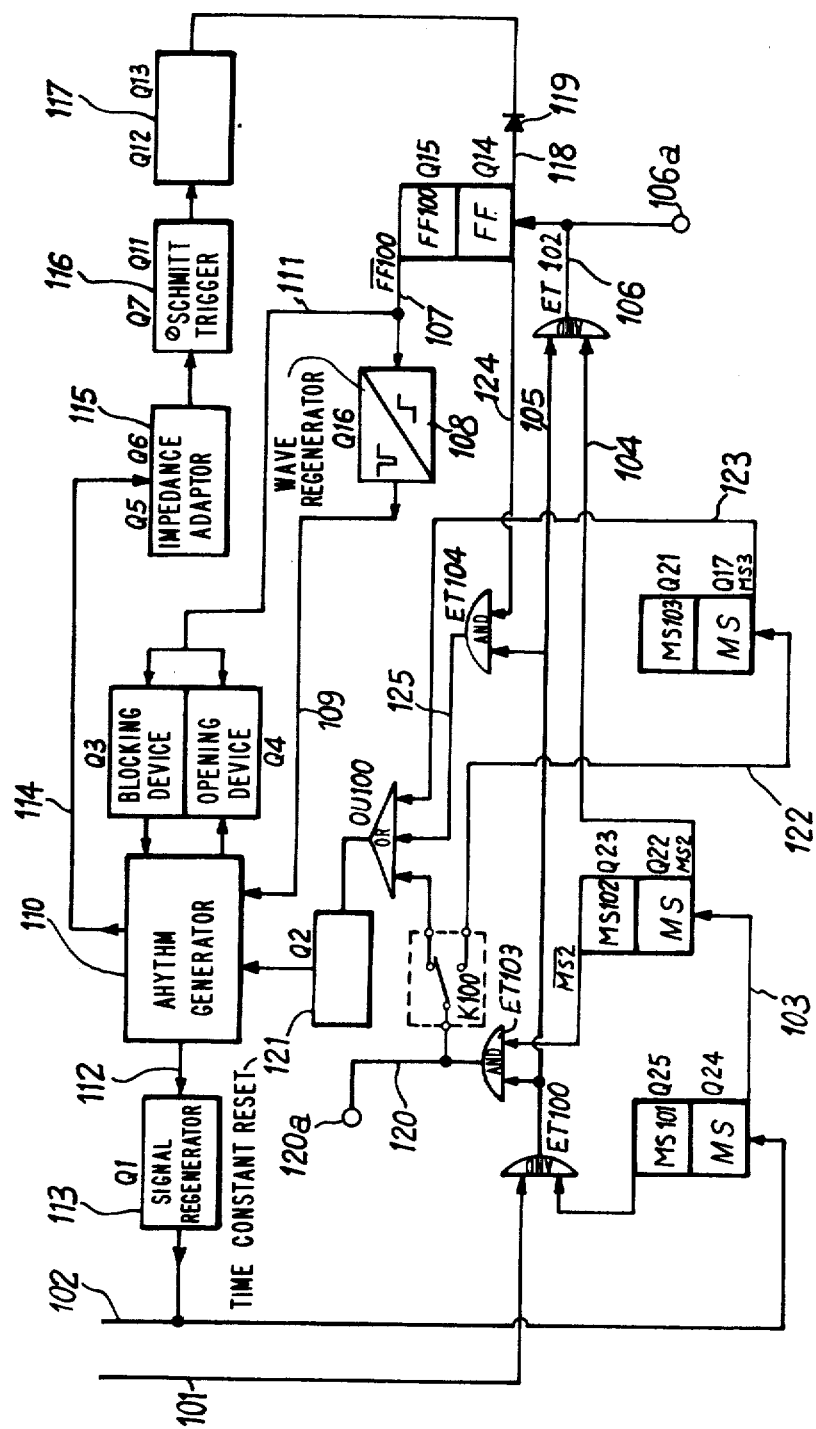
FIG. 12 is another embodiment of the apparatus of part A.

In the third embodiment which will now be described (FIGS. 12, 13 and 14), the capacitance of the time delay means also forms part of the time base and the charging resistance R11 of this capacitance is common to the time base and to the means for changing the state of the time delay means.

It will be seen that the device according to the invention comprises a cardiac detection electrode 101, the conductor of which leads to the input of a gate ET100, the second input of which is connected to a monostable MS101 (which may be adjusted between 300 and 400 milliseconds). The input of this monostable is connected to the conductor of a cardiac stimulating electrode 102. The monostable MS101 is also connected through a conductor 103 to a monostable MS102 which is adjustable for example between 300 and 600 milliseconds MS102 being excited for the corresponding period by the return of MS101 to its stable position. One of the outputs of MS102 leads through conductor 104 to the gate ET102. The output 106 of the gate ET102 makes it possible to switch a flip-flop FF100, the output 107 which is connected to wave regenerating means 108 (containing the transistor Q16) for transmitting a signal to the rhythm generator 110 which will be hereinafter described in detail.

The pulses from 108 through the conductor 109 permit the abrupt discharge of the capacitance of the rhythm generator 110. On the other hand, the output 107 of the flip-flop is connected by a conductor 111 to both a transistorized blocking device comprising the transistor Q3 and to a opening device comprising the transistor Q4. The rhythm generator 110 is connected on the one hand through an output 112 to a signal regenerator 113 which transmits the stimulating pulses from said rhythm generator 110 to the stimulating electrode.

On the other hand, an output conductor 114 of the rhythm generator 110 responsive to the potential of the condenser of the rhythm generator leads through an impedance adaptor 115 to the transistors Q5, Q6, to a Schmitt trigger 116 which is connected through a potential aligner 117 to an input 118 of the flip-flop FF100. A diode 119 in the conductor 118 makes it possible to make the flip-flop FF100 responsive only to the trailing edge from the trigger.

Figure 13:
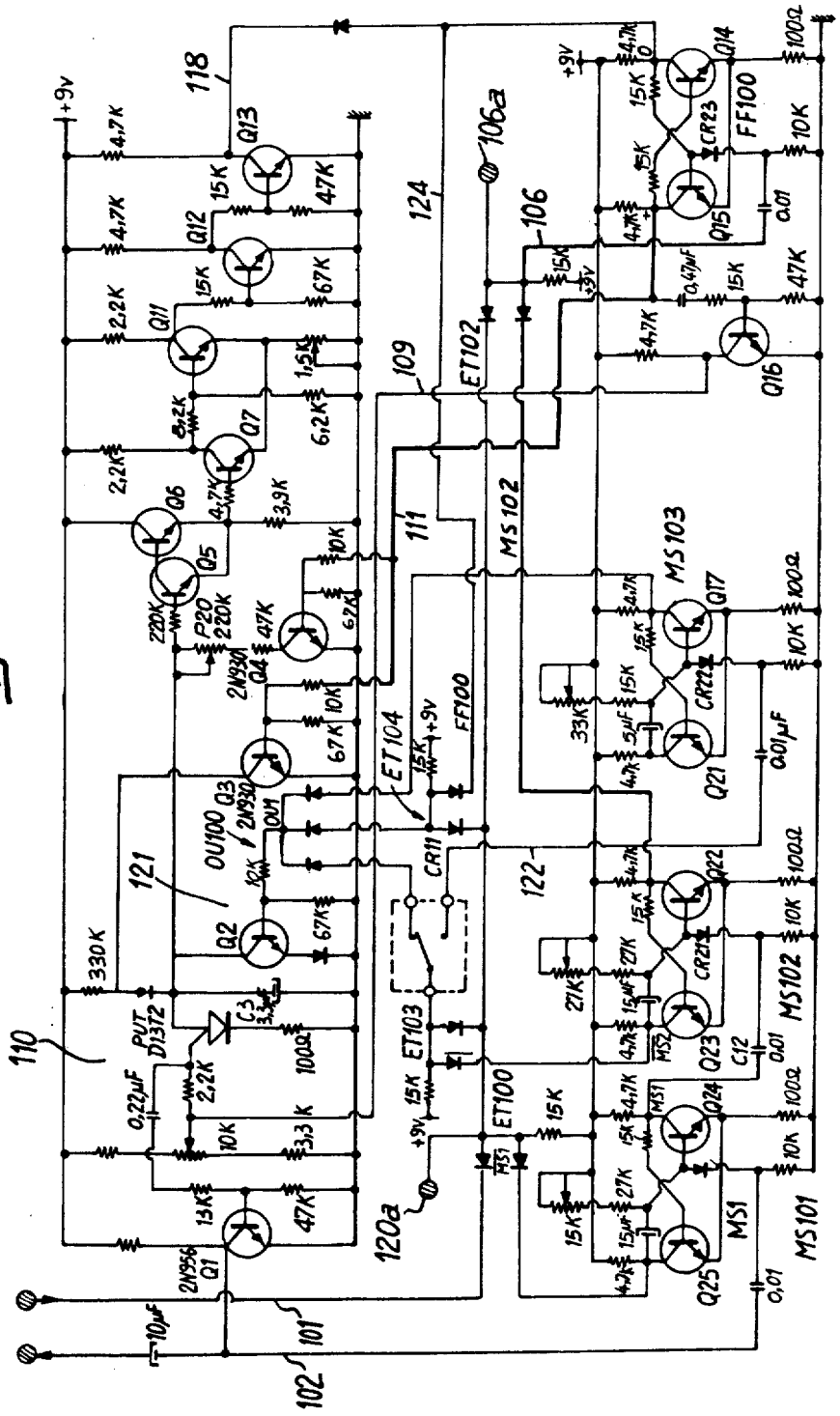
FIG. 13 is a circuit diagram of the device shown in FIG. 12.

As will be seen by referring more particularly to FIG. 13, the condenser C3 of the rhythm generator, charges if no pulse comes along the conductor 101, and after a certain lapse of time, 800 milliseconds in the present example, the condenser reaches a potential such that it acts on the programmable unijunction transistor PUT of the generator to simultaneously suddenly discharge the capacitance and transmit a stimulating pulse along the conductor 102. The transmission of this stimulating pulse swings MS101 to its unstable position so as to block the gate ET100, for example, for 300 milliseconds. No signal received along 101 can, during this period, be admitted into the device.

After this period the return of MS101 to its stable state results in the opening of the gate ET100 and (through conductor 103) in the switching of MS102 into its unstable position. This opens the gate ET102 for the period indicated on MS102. If an extra-systole SS detected on 101 takes place at this moment the corresponding pulse passes through ET100 and ET102 which is now open, to reach FF100, which is switched as may be seen on FIG. 14. This switching movement is sensed through the conductor 111 which, acting on the transistors Q3 and Q4, causes the capacitance C3 to discharge, not suddenly this time, but instead slowly into the potentiometer P20. The condenser thus discharges slowly as will be seen in the descending phase of the schematic line representing the evolution of the potential of the time base.

On the other hand, each increase in the potential of the capacitance C3 causes, when the capacitance has reached a sufficient potential, corresponding for example to 250 milliseconds of charging, the switching of the Schmitt trigger 116, as may be seen on FIG. 14. This trigger switches again to return to its initial position, for example, during the abrupt discharge of the capacitance C3 at the end of the predetermined period of 800 milliseconds if no spontaneous systole has been detected.

On the other hand, the Schmitt trigger returns to its initial position during the discharge through the potentiometer P20 when the potential of the capacitance C3 has decreased to a predetermined value. The trailing edge then passes from the Schmitt trigger 116 through 117 and switches the flip-flop FF100. At this moment the corresponding signal on the output 107 is transmitted by 108 to the time base 110, the remaining potential of which is abruptly discharged. When the capacitance discharges slowly the switching of the trigger causes the abrupt discharge of the remaining potential of the remaining capacity as well as the transmission of a corresponding stimulating pulse through 113 and 102.

At this moment the stimulating pulse I received at 102 again closes the gate ET100 through MS101 and a new waiting cycle begins. It will thus be easily seen that the sooner the spontaneous systole takes place, the less the potential of the capacitance C3 will be increased and the more rapidly during the discharge into ET102 the switching potential of the Schmitt trigger will be attained. The response of the device according to the invention is thus quicker when the spontaneous systole is premature. It follows that by suitably adjusting the charging resistance R11 and the discharging resistance P20, the stimulation period may be modified to operate in a relaxed manner, that is to say without being subjected to the influence of the systoles and the rapidity of the discharge into the potentiometer P20.

In accordance with another characteristic, the device according to the invention may be adapted to retard the waiting period when the spontaneous systoles are not premature, but take place a little before the normal time for a new stimulating pulse (in the absence of the detection of a spontaneous systole). It should be noted that this effect may, in a first approach, be obtained by simply adjusting the charging resistance R11 and discharge resistance P20 of the capacitance C3 in such a manner that if a dangerous systolic pulse takes place just at the end of the dangerous period (just before the closing of ET102), the discharge attains the switching potential of the trigger after a period equal to the normal period during relaxed operation of 800 milliseconds.

However, according to this other characteristic of the invention, the device preferably comprises a gate ET103 connected on the one hand to the output 105 of ET100 and on the other hand to an output of MS102 which inhibits this gate when ET102 is open. Once the gate ET102 is closed, that is to say after MS102 returns to its stable position, the gate ET103 opens and, if a delayed spontaneous systole SS takes place, it passes through the gate ET103, the output 120 of which is connected to a switch K100. In one of the positions shown on FIG. 12 the corresponding pulse passes to gate OU100 and reaches a transistor Q2 for resetting the time constant to zero. (This carries reference number 121 on FIG. 12).

As may be seen on FIG. 14, the actuation of 121 resets the rhythm generator to zero, but this time without causing the simultaneous transmission of a stimulating pulse to the conductor 102. In conclusion, after a spontaneous systole which is not premature has taken place, the capacitance again charges and the waiting period of 800 milliseconds begins again, in the absence of any new spontaneous systole.

However, by switching K100 to its second position, the pulse, instead of being directly transmitted to the gate OU100, is lead by a conductor 122 to a monostable MS103 which is adjustable or variable, for example, between 50 and 150 milliseconds, and which, when it is actuated, maintains the potential of the capacitance of 110 at zero during the corresponding 50 to 150 milliseconds, this always through the gate OU100 and the conductor 123. In this latter case the delay after a spontaneous delayed pulse is greater than the predetermined period of 800 milliseconds and is, for example, equal to 950 milliseconds if MS100 is adjusted for 150 milliseconds.

In accordance with another characteristic of the invention, the conductor 105 has another output connected to a gate ET104, the second input of which is connected to the flip-flop FF100 through the conductor 124, the output 125 of this gate being also connected to OU100. Thus, through 124, this gate ET100 is open only when the flip-flop FF100 has first switched into its non-normal position, that is to say, if a dangerous spontaneous systole has already passed the gate ET102. The gate ET104 then remains open until the trigger 116 has swung FF100 again to its initial position as previously seen. If during this period a new spontaneous systole occurs, which is directly consecutive to the preceding spontaneous systole and passes through ET100, the corresponding pulse passes then through the gate ET104 and through OU100 reaches 121 which cancels out the potential of the capacitance C3 without the emission of an artifical stimulating pulse. Thus in the case of tachycardia the operation of the apparatus as a whole is blocked, on condition however that the spontaneous systoles succeed each other at a more rapid rhythm than the response of the device by discharge into P20.

It is however possible to provide, in addition to manual regulation of the potentiometer P20, which makes it possible to adjust the rate of discharge, and thus the waiting period after a dangerous systole, an automatic device acting for example on P20, to increase the rate of discharge when sequences of several dangerous systoles persist. It is then possible, for example, to use a supplementary capacitance adapted to determine from the charging potential the time separating two consecutive spontaneous systoles, the level of the charging potential attained in ths capacitance acting on an electronic device which varies P20 in an appropriate manner. In this case P20 is preferably replaced by several different resistances in parallel which are actuated by electronic blocking devices such as transistors.

Means may also be provided to return the value of P20 to its initial value at the end of a certain period of the trains of dangerous systoles have disappeared.

It is also possible, in a variation, instead of transmitting a single stimulating pulse during the discharge of C3, to send two consecutive stimulating pulses automatically by means of a suitable pulse generator controlled by the device 110. Finally, it is also possible to vary the voltage of the stimulating pulse as a function of the rapidity of response of the stimulator according to the invention. Thus, the stimulating voltage will remain constant during normal operation without apparition of a spontaneous systole. On the contrary, this voltage will increase, in the case of the apparition of extra-systoles, to the extent of the increase in the speed of response of the device, that is to say, in relation to the prematurity of the extra-systoles.

As a practical matter, this relationship may be obtained by interposing between the source of stimulation and the device 110 an electronic device which increases the voltage of the stimulating pulse when the charging potential obtained during the occurrence of a systole decreases, that is to say when the systole SS is more premature.

Moreover, these different devices may be combined with a hemodynamic detector which, when the establishment of the sanguine pressure is slower, also makes it possible to increase the stimulating voltage.

The device according to the invention may also comprise several different devices or suitable connections, such for example as a tapping 120a at the output 120, in order to make it possible to count the delayed extra-systoles SS, whereas the outlet 106 of ET102 may comprise a tapping 106a for counting the dangerous extra-systoles. These different outputs may be used in association with a device for changing the frequency of the rhythm generator.

It will be appreciated that the device according to the invention may be advantageously implanted in the body because it comprises a very small number of electronic units and requires a very small consumption of energy. Finally, the monostables MS101, MS102 and/or MS103 may be replaced by other devices adapted to momentarily block the gates. These devices may even be directly controlled through programmable transistors by the potential of the capacitance C3 of the device 110.

Finally, a device according to the invention may comprise a second capacitance analogous to C3, which is connected by a suitable device to the output of the gate ET102 so as to begin charging through a charging resistance only if a dangerous systolic pulse passes the gate ET102. If after this systole a new directly consecutive systole appears through ET102, said capacitance discharges in a discharge resistance to cause a stimulation, after which the potential decreases to a predetermined base value. If no second systole takes place, this capacitance discharges abruptly without causing a stimulation.

OTHER EMBODIMENTS OF THE INVENTION

By way of example, other embodiments are given below.

The first of these makes it possible to provide for discontinuous variation of the waiting period Y, which may have two values, one equal to the value of the stimulating period X, and the other less than X, the lower value of Y being established for the systoles which are closest together. This embodiment is illustrated on FIG. 15. Referring now to this Figure, it will be seen that the device according to the invention comprises the detector-conductor 8 which leads to a first gate ET301, a branch 321 of the conductor 8 leading to a second gate ET302, the output of ET301 and that of ET302 leading to a gate OU300, which leads to a pulse generator A300 forming the time base and normally delivering stimulating pulses I separated by predetermined period, for example 900 milliseconds. This is brought about through the conductor 326 which controls a power device P300 leading to the stimulation conductor 11. A conductor 310 leads from 11 to a monostable MS301 which blocks the gate ET301 for a period of 750 milliseconds after each stimulation by 11. During these 750 milliseconds, MS201 through a conductor 312, opens the gate ET302 which is closed by MS301 when the latter is returned to its stable state after the 750 milliseconds. A second branch 313 leads from 11 to a monostable MS302 which, through a conductor 314, closes ET302 for the first 400 milliseconds which follow a stimulation by 11. Thus after the transmission of a stimulating pulse I, the gate ET301 is closed for 750 milliseconds and the gate ET302 is closed for 400 milliseconds and opened for the following 350 milliseconds and reclosed during the 150 last milliseconds of the predetermined period of 900 milliseconds. The output of ET302 also leads to a delay device B300 which, when a signal passes through ET302, transmits through its own output 315 a pulse or signal which controls P300. A branch 316 leads from 315 to the gate OU300. A conductor 325 may also be provided which leads from the conductor 8 to the control electrode 310 of MS320, together with a second conductor 327 which does the same for MS302. The operation is as follows:

If, after stimulating pulse I, a systole SS takes place during the first 400 milliseconds, the device does not react. If SS takes place between 400 and 750 milliseconds, the gate ET302 is open and, through OU300, the signal returns the time base A300 to zero. This base is preferably a time base comprising a condenser which charges and which, having attained a certain potential, discharges abruptly while actuating B300 throughout the 900 milliseconds. Such a time base is similar to those which have already been described.

In like manner the electrical signal which comes from ET302 reaches B300 which, after a time delay, for example 600 milliseconds, transmits a signal over 315 and produces a stimulation I over 11. At the same time, through 316, the time base A300 is reset to zero.

If now, before B300 has actuated P300, that is to say before the end of the time delay of 600 milliseconds, a new spontaneous systole takes place, the second spontaneous systole passes through the gate ET302 which is always open and resets A300 to zero while starting B300 for a 600 millisecond waiting period.

The device B300 may preferably comprise a monostable set for 600 milliseconds. In order that it will not operate when, having been started by a first spontaneous systole, a second spontaneous systole takes place before 600 milliseconds, B may comprise a suitable device, for example a flip-flop adapted to inhibit through an inhibiting transistor the 600 millisecond monostable. This flip-flop may be switched by the first spontaneous systole into a position which permits the 600 millesecond monostable of B300 to operate but, when a second spontaneous systole passes through the gate ET302, is switched to inhibit B300. This stimulation reswitches the flip-flop into its original state on non-inhibition.

Of course the device B300, instead of comprising a single 600 millisecond monostable, may, for example, comprise a plurality of monostables, a plurality of gates such as ET302 being provided which are successively opened one gate at a time, for example the monostables such as MS301, MS302, which are triggered by the stimulation. In this way, when a spontaneous systole takes place, it will be switched to the delay monostable corresponding to the gate which is open at this moment. Other explanations are unnecessary, such an embodiment being easily derived from the teaching of the various examples hereinbefore described.

Referring now to FIG. 16, this represents an embodiment utilizing digital means.

This device comprises principally a source of pulses, a counter, and a memory which, as a function of the number of pulses counted during the period K, controls the delay Y before stimulation. As seen on FIG. 16, the detector conductor 8 leads to a flip-flop FF400 which it switches, and which may be switched back by a stimulating conductor 411 controlling a power device P400 transmitting the pulses to the stimulation conductor 11. The device comprises an adder-subtracter C400 which may be alternatively placed in an adding or subtracting state, depending upon the position of the flip-flop FF400, through the conductors 401 and 402. The flip-flop FF400 constitutes the means for memorizing the number of pulses counted, as will be seen below.

The device comprises a time base 414 which is in fact a pulse generator transmitting pulses at a fixed frequency to the adder-subtracter C400. Such pulse generators are well known. During the predetermined period X, for example 1000 milliseconds, 414 emits 100 pulses, that is to say one pulse 10 milliseconds. In this embodiment, the pulse generator 414 never stops. The operation is as follows:

A stimulating pulse I has just been transmitted to 11. The counter C400 is in counting position. It counts all the pulses which have been transmitted to it by 414 and, at the one hundredth pulse counted, resets itself to zero, as is well known in adder-subtracters, by transmitting a pulse which, through 411, assures the stimulation, and the same cycle repeats. If a spontaneous systole then takes place before the 100th pulse counted, which systole passes through the conductor 8, this systole swings FF400 into the position in which, through 402, places the counter C400 in the subtracting state. From this moment, C400 subtracts from the number which it has counted at the moment at which FF400 was switched the subsequent pulses from 414. If for example, this spontaneous systole takes place at 600 milliseconds, the counter has counted 60 pulses and it must then subtract all the new pulses until it reaches zero. At this moment C400 actuates P400, which emits a stimulating pulse. It will be understood that in this case the delay period Y is strictly equal to the interval A, this is to say, in the specified example, 100 milliseconds. By actuating P400, C400 is caused at the same time, through 411, to switch FF400 to return it into the adding state. Of course, the device may comprise different means for detecting and selecting the systoles which arrive through 8. Those means may be identical or similar to those described in the preceding examples, and may comprise for example gates opened by monostables or by counters.

In a variation of this device it is possible to have a delay period Y different from the interval K which causes it. In this variation a second pulse generator 412 of a conventional type is provided. This pulse generator 412 is capable of transmitting to C400, for example, 100 pulses per 1000 milliseconds. These pulses are not separated by equal intervals as in the case of the generator 414, but on the contrary by regularly decreasing intervals. Thus, by way of example, 412, during the 100 first milliseconds of its operation, generates four pulses and then generates five in the next 100 milliseconds and so on. The operation is then as follows. The counter C400, having counted the pulses which were transmitted to it by 414, is placed in the subtracting state as hereinbefore seen, under the influence of the spontaneous systole which swings FF400. Simultaneously, FF400, through the conductors not shown, blocks the pulses of 414 from reaching C400 and starts the pulse generator 412, and the counter then subtracts the pulses which have been transmitted to it. If, for example, C400 had recorded 60 pulses coming from 414 it must then take a longer time to subtract them, from 412. Once all the pulses have been subtracted, the stimulation takes place and the flip-flop having reswung, 414 again transmits its pulses to C400.

In this variation, the delay means consists of the counter C400 and the pulse generator 412, and the flip-flop and the means for changing the state comprise the counter C400 and the pulse generator 414. The state of the delay means is the number of pulses counted.

DESCRIPTION OF DEVICE C

The device A of the heart pacer type according to the invention, which makes it possible to produce a variation in the waiting period Y on the demand of the cardiac muscle, may advantageously be associated with the device C adapted to carry out a process for varying the frequency on demand.

In accordance with the invention this process consists on the one hand, in periodically adding a given number of cardiac systoles detected by the electrodes 2, for example 12 systoles (that is, of all the systoles, both those which are spontaneous and those which are provoked by the stimulation), and on the other hand while this predetermined number of systoles is being counted, also counting a predetermined, obviously smaller or at most equal number of spontaneous systoles presumed to be dangerous, for example premature extra-systoles. This predetermined number of dangerous systoles may be for example, four. If such a number is counted, the frequency of cardiac stimulation is temporarily increased, that is to say X is decreased.

This process is started by the device C, which may be used alone or in association with the device A. Association with A is preferably because in this case the device C need not have detecting means and selecting means adapted to select the spontaneous systoles deemed to be dangerous for counting, the latter being transmitted directly through the selecting gate, such as ET2, ET02 of the devices A alread described. Moreover, if the device C operates independently, it temporarily increases the frequency of caridac stimulation from the point at which, among a predetermined number of systoles, for examples 12, it has counted four dangerous systoles, whereas when it works in combination with the device A, the dangerous systoles are for the most part eliminated by the variable waiting period Y, and it is only when the device A is insufficient to suppress the too frequent apparition of dangerous extra-systoles that the device C operates to temporarily increase the frequency, for example for a period of 10 to 20 seconds. The frequency may then pass from 60 pulses per minute to 90 pulses a minute. Of course, this specific increase in frequency is given purely by way of example and it is even possible to provide a device C in which the temporary increase in the frequency takes place in several steps, the frequency being first increased for a certain time from 60 to 80 pulses per minute and then, if that is insufficient, from 80 to 100, and so on.

In the specific embodiment described below, the waiting period Y is not variable once C stimulates with its higher frequency. The stimulation from C suppresses the stimulation from A.

After having reached the device A, the systole detector conductor 8 passes to the device C, making it possible to temporarily modify the cardiac frequency stimulation if spontaneous dangerous extra-systoles appear. In this device C, the conductor 8 leads to an integrator 512 of a conventional type, known as a step-by-step integrator. This integrator delivers a potential which increases in a discontinuous fashion like stair steps, each pulse from the conductor 8 increasing the potential of the integrator by one step. At the end of the 12th step, this is to say the 12th systole, the potential of the integrator resets itself automatically to its initial value and simultaneously the integrator emits over the conductor 513 a reset to zero pulse the path of which will be hereinafter described. This integrator 512 constitutes the systole counter, regardless of whether the systoles are spontaneous or stimulated.

Another conductor 514 from the device A enters the device C. This conductor 514 is traversed only by pulses corresponding to premature cardiac spontaneous systoles which are believed to be dangerous. The device A directs over the conductor 514 only the premature dangerous spontaneous systolic pulses by opening a gate such as ET2 or ET02, (open for example from 400 to 700 milliseconds after an electro systole ES). The conductor 514 leads to a gate ET4, the second input 515 of which is connected to the output of a flip-flop FF4, the conductor 515 normally opening the gate ET4 when the flip-flop FF4 is in the corresponding state. The gate ET4 leads through a counter 516, represented on FIG. 2 inside a broken line. This counter 516, which counts the premature spontaneous systolic pulses, comprises for example two flip-flops FF2 and FF3 as well as a decoder DD the function of which will be hereinafter explained. The decoder has four outputs connected to a multi-position rotary switch K10, which switch may be pre-actuated manually, or automatically, or by remote control when the device is implanted in the body of the patient. The multiposition switch K10 is connected by a conductor 517 to one of the inputs of the flip-flop FF4. The output 515 of flip-flop FF4 is also connected to two inhibiting transistors A10 and A20. When the flip-flop FF4 is in its normal state, the inhibitor A20 prevents the operation of a time base, for example an integrator 518 which, when not cut out, integrates a potential over a period of 15 seconds, after which its potential falls to its original state and a pulse is emitted over the output conductor 519. When the flip-flop FF4 is in its normal position, the inhibitor A10 prevents the operation of an integrator 520, which is a pulse generator transmitting pulses at a predetermined frequency over the conductor 511, said stimulating pulses controlling the stimulator 10 (see FIG. 2) which transmits a stimulating pulse to the cardiac electrode for each pulse received by 11.

As will be seen on the drawing, the pulse generator 520 may preferably be adjustable, and the frequency delivered may be regulated for example between 90 and 150 pulses per minute. However, it is also possible to use a non-adjustable generator which delivers only a single frequency. In any case, the lowest frequency capable of being transmitted by the integrator 520 must be greater than the stimulating frequency of the heart pacer A or of any other cardiac stimulating device associated with the device C according to the invention.

The operation of the device C is as follows:

The integrator 512 being in starting position, its potential increases one step at each pulse from the conductor 8 engendered by a systole, regardless of whether it is a spontaneous systole SS or an artificial systole ES, detected by the electrode 2. At the end of the 12th systole counted, the integrator 512 returns to its starting position and emits through a conductor 513 a pulse which, passing through a gate OU20 and pulse regenerator EF then returns to zero the counter 516 for premature spontaneous systoles. If a dangerous premature spontaneous systole takes place, it is normally counted in the integrator 512, but at the same time a pulse passes through the gate ET4 and the conductor 514, and this pulse is counted 516 for premature spontaneous systoles. When it is not believed that the frequency of artificial cardiac stimulation need be increased until at least 4 premature spontaneous systoles take place during a cycle of 12 systoles, the rotary switch K10 is placed in position 4 and the counter 516 does not send a pulse to 517 unless it counts four pulses from 514 before being reset to zero by the conductor 513. Thus, 512 counts all the cardiac systoles, whereas 516 counts only the dangerous spontaneous systoles, for example those having passed through the gate ET2 if the device A is that of FIG. 3. Of course, instead of having four outputs, the device 516 for counting premature spontaneous systoles may have a different number of outputs. On the Figure, the rotary switch K10 is represented in the position closing the circuit to the output 1, which amounts to saying that a pulse will be transmitted through 517 to FF4 when a pulse enters 516 through the gate ET4. The operation in this position, in which the counter counts only a single pulse, does not correspond, in general, to the usual operation of the device according to the invention, since in this case the device C temporarily increases the frequency of stimulation when a single premature spontaneous systole appears.

When the means 516 for counting premature spontaneous systoles has counted the required number of premature spontaneous systoles before being reset to zero by the lapse of the integrator 512, a pulse will be emitted by the output 517 of the counter 516 to swing the flip-flop FF4. By departing from its normal position, this flip-flop renders the transistors A10 and A20 conductive, through its output 515, so that the time base 518 and the pulse generator 520 begin to operate with the generator 520 controlling, as has already been said, the transmission at the desired frequency of cardiac stimulating pulses to the cardiac electrodes 2. During this time the second output 521 of flip-flop FF4 acts on a transistor A30 which inhibits the integrator 512, which is thus returned to its initial potential and kept in this position while FF4 remains in its swung position. At the end of 15 seconds, the potential of the integrator 518 falls and it emits a pulse through the conductor 519, which pulse is transmitted through the gate OU20, on the one hand, by means of a counter 516 which is then reset to zero and, on the other hand, by means of a conductor 522, to the second input of the flip-flop FF4, which is thus switched back and reset to its initial position, which has the effect of stopping the integrator 518 and the pulse generator 520, and thus of suspending the cardiac stimulation by this time base and at the same time releasing the integrator 512 so that the device B returns again to its waiting position to detect and count pulses coming from dangerous premature spontaneous systoles, as before.

Referring more particularly to FIG. 18, it will be seen that the means for counting premature spontaneous systoles 516 comprises, in addition to the gate ET4, two flip-flops FF2 and FF3 associated with four gates, ET5, ET6, ET7 and ET8, the four outputs of which lead respectively to the four conatacts of the rotary switch K10. Such decoders are already well known and it is not necessary to explain their functioning in detail.

As may be seen on FIG. 18, the operation of this counting means is as follows:

The flip-flop FF2 is swung by the trailing edge of the electro-systole from the gate ET4. Since counter 516 has been returned to zero, the first pulse passes through ET4, and travels toward the gate ET5 through which it may pass, becuase the two other inputs of this gate ET5 are validated by the corresponding outputs of FF2 and FF3 which are both at a positive potential. The three other gates of the counter 516 are, on the contrary, closed because one of their inputs at least is invalidated. The pulse passes through the gate ET5 and reaches terminal number 1 of the rotary switch K10. If the rotary switch is set at this terminal, the pulse is then transmitted to FF4. If it be supposed that the rotary switch is, on the contrary, set at the contact 4 of K10, nothing passes through the conductor 517 and the only change in the device will have been the switching of FF2. If, now, a second dangerous systole takes place, its trailing edge swings FF2 to return it to its initial position. During this operation the negative edge switches FF3 which has been regulated so as to be responsive to the negative edge from FF2. At this moment it is the gate ET6 which is open. Once the pulse passes through the gate ET6 this gate is closed by the switching of FF3 and it is then the gate ET7 which is open to permit passage of a possible third premature spontaneous systole. If a fourth premature systole takes place before the device 516 has been reset to zero by the integrator 512, this systole will leave through ET8, since it has been opened, at the end of the preceding pulse, by switching FF2. K1 being in position 4, a pulse will pass to FF4 when the four pulses have been counted.

It is, however, obvious that the means such as 516 for counting premature spontaneous systoles may be quite different and it is not necessary to be able to change, during use, the predetermined number of premature spontaneous systoles which are to be counted, to act on FF4. This number may be determined in advance, and particularly in the case of an implanted cardiac stimulating device.

It is, on the other hand, possible to provide, in the device B, a push button stop K3 capable of grounding a conductor 528 which, when grounded, returns the flip-flops FF2, FF3 and FF4 to their initial state. It is thus possible to reset the pulse generator 520 to zero if that is operating, without waiting for the fall of the integrator 518. The actuation of the button K3 thus resets all the assembly B to its initial position.

A second button K2 makes it possible, on the other hand, to operate on the input of flip-flop F4 in the same way as if it had been actuated by a pulse from the conductor 517. This button K2 makes it possible to start the pulse generator 520 without waiting for the production of a dangerous premature spontaneous systole. In the case of an implanted device, the contact K2 may be closed, for example by remote control. Finally, a double contact K4 may permit either the opening of the inhibiting circuit of transistor A10 and the grounding of the conductor 528, or, on the contrary, leaving the inhibiting circuit closed and isolating the conductor 528 from ground. In the first case, the contact K4 permits continuous operation of the pulse generator 520, which may comprise a transistor PUT(programmable unijunction transistor) while maintaining the remainder of the device B in the reset state by grounding the conductor 528. The device such as C may also be used to initiate operation of the time delay means only when it detects a given number, for example at least 2, of dangerous systoles SS among the predetermined number of systoles counted in 512, (for example 12 systoles). In this case FF4, instead of being connected to the time base 520, is connected to a device which imposes a predetermined delay X even though two systoles dangerous SS have not been counted in 516. In this case, the first dangerous systole SS is followed by a time delay equal to X, and the second by a delay Y.

Referring now to FIGS. 19, 20 and 21:

In one variation of the invention certain parameters of the response of A, or B, may be controlled from a device responsive to the intramyocardial pressure. Thus, for example, the voltage of the stimulating pulses 1, or the period X, or the ratio Y/K may be automatically modified in response to variation of the intramyocardial pressure.

By intramyocardial pressure is meant not the abrupt variations resulting from cardiac systoles or respiration, or other organic movements, but on the contrary, the variation of the average base pressure, measured for example during the time of rest of the cardiac muscle. This variation, when it occurs, is very slow, and may be detected only after several hours in certain cases. The device for detecting the intramyocardial pressure is characterized by the fact that it comprises a microdetector of pressure, a liquid such as polyvinyl-pyrolidone, at least partially surrounding said microdetector, a flexible envelope for holding said liquid, and one or more conductors, preferably electrical conductors, connecting the microdetector to the device A.

The microdetector may be of a known type which will be described in greater detail by way of example in the following.

The envelope may be made either of a very fine mesh cloth made with fine flexible threads, for example of a textile material, glass or metal or any plastic material, or a thin membrane which may be porous or impermeable and made of an elastomer or a plastic material. When the envelope is made of cloth, or a permeable membrane, the liquid used will be a non-wetting liquid which has no tendency to diffuse in the envelope or in the environmental organic matter.

The device according to the invention makes it possible to detect or measure the intramyocardial pressure and is positioned preferably on a brance 601 of an intraventricular catheter 602. This intraventricular catheter 602 carries two electrodes 603 and 604 normally permitting cardiac stimulation. The branch 601 may also carry an electrode 605 cooperating with the electrode 602 and capable of being actuated if it is discovered that the electrode 603 no longer functions, by establishing that the stimulations are not followed by a systole. The branch 601 penetrates the intraventricular septum 606 and leaves, for example, by the left ventricle 607. A blood pressure detector 608, may, for example, be attached to the end of the branch 601. The catheter forming the branch 601 comprises, in accordance with the invention, an intramyocardial pressure detector 609 which comprises a microdetector of pressure 610, for example of the type sold by the Statham Company, positioned inside a liquid 611. A conductor 612 makes it possible to transmit information from the detector 610 along the catheter to the at least partially implanted device (not shown). The liquid 11 is contained in the envelope 613, which is extremely flexible.

It is nevertheless possible to avoid the installation of a fibrous layer around the envelope 613 by surrounding it with a layer of veinous tissue of conjunctive tissue belonging to the person equipped with the device according to the invention. It is even possible to make the envelope 613 from a small portion of vein closed at its two ends.

The insertion of the pressure detector 609 into the intraventricular septum may be made by means of catheter comprising an external tube 614, the end 615 of which pushes in front of it the head 608. Once the head 608 has been brought into a good position, for example inside the left ventricle 607, it suffices to withdraw the outer tube 614, leaving the inner branch 601 in place. If it is desired to utlimately withdraw the branch 601, it is possible to provide on the envelope 613 reinforcing means 616, for example metallic wires, so as to transmit the tractive forces which result from the operation of withdrawing the branch 601, thus avoiding any risk of tearing the envelope 613. Of course, it is possible to position the envelope 613 in another location with respect to the branch 601 without departing from the basic principles of the invention. In like manner, the detection of the intramyocardial pressure may be made in other places than in the intraventricular septum, even though this latter positioning is preferable because the septum is easily traversed without any ill effects on the cardiac muscle.

Figure 15:
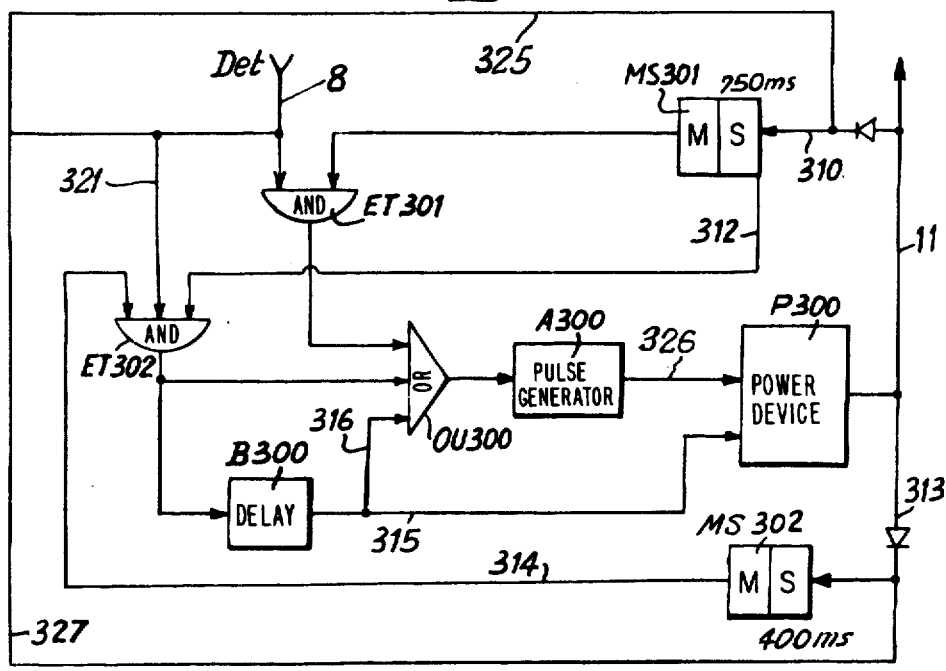
FIG. 15 shows another embodiment of the part A.

There will now be described, with reference to FIGS. 22 and 23, a device constituting an improvement over the device A of the second form of the preferred embodiment, but which may also be utilized with the other embodiments of the device according to the invention illustrated on FIGS. 3, 15 and 17.

The device which will now be described makes it possible, when a second consecutive spontaneous systole occurs after a first spontaneous systole, to institute on the occurrence of this second spontaneous systole, a new waiting period, this time variable in accordance with the process according to the invention, and no longer fixed as has been the case in the devices hereinbefore described. This improvement is obtained principally by doubling the time delay means so that one time delay means institutes a variable waiting period according to the process according to the invention upon the occurrence of a first spontaneous systole, whereas the second delay means changes state as a function of time so as to be able to furnish, in the case of a second directly consecutive spontaneous systole, a new time delay period which is variable in accordance with the process according to the invention. In the device described, the delays or waiting periods Y are preferably less than the intervals of time K which cause them, so that such devices make it possible to intervene very efficaciously against the tendencies of the heart to take up a tachycardial rhythm. In the description of the device which will now be given, a variable waiting period according to the process of the invention is instituted for all the spontaneous systoles which successively succeed another, but in the simpler devices it will be appreciated that one cannot make a supplementary variable waiting period start until the second spontaneous systole occurs, and the third consecutive spontaneous systole returns the apparatus to a waiting period of fixed duration, for example equal to X, as is the case with the devices hereinbefore described.

More particularly, the device described in FIG. 22 comprises, on the detector conductor 8, a gate ET700 capable of being closed for a short period by a monostable MS701 actuated by the stimulating conductor 11 when stimulating pulses I are transmitted, so as to prevent the systole created by this stimulation from penetrating into the device. A second monostable MS702 is provided to close the gate during a period, for example equal to 300 milliseconds, after the detection of a systole, whether it is spontaneous or not. The output 701 of said gate leads, on the one hand, to a device D701, and on the other to a device D702, these two devices being directing means which are for example in the form of voltage dividers. Thus, when a spontaneous systole SS takes place, it passes through the gate ET700 thus interdicting it for a period greater than the refractory period predetermined by MS702, and then reaches D701 and D702. D701 has two outputs, 702 and 703, whereas D702 has two outputs 704 and 705. If a pulse coming from 701 is directed, by D701, to the conductor 702, then the pulse will also be directed by D702 to the conductor 705. Alternatively, it will be directed by D702 to 704 if it is directed to 703 by D701. The dividers D701 and D702 are also reversed simultaneously through branches (not shown) from the conductors 721 and 722 when any stimulating pulse I occurs on one of these two conductors. Thus, if the divider D701 has transmitted a first pulse to 702, it is automatically placed in a position for transmitting the following pulse to 703. If, however, a stimulating pulse I appears on 721 before a second spontaneous is intended to pass to 703, then D701 is returned to its initial state and the next spontaneous systole passes via 702.

The conductors 702 and 703 lead respectively to two devices HV, HV' which are identical with each other and, for example, identical to the device HVa illustrated in detail on FIG. 8. When a pulse arrives over 702 it discharges HV through its discharge resistance, and at the end of this discharge HV transmits a stimulation through 721 to the power device P700 which amplifies it and transmits it over the stimulation conductor 11 as has already been seen. It is the same for HV' if the spontaneous systolic pulse comes from 703. Moreover the devices HV and HV' may be inhibited, that is to say, the potential of the capacitance may be maintained at zero, by inhibiting transistors I700 and I'700 actuated either for a short time by the lead 713 and 712 of the conductors 703 and 702, or for a longer time by the flip-flops FF701, FF702, respectively, switched into the inhibiting state by the stimulating pulses from the conductor 722, 724 for the first of them and from the conductor 721-723 for the second. The flip-flops FF701, FF702 may be switched back into non-inhibiting positions by the conductors 704 and 705 respectively. The operation is then as follows:

Let is be supposed that, as shown on FIG. 23, FF702 inhibits HV', then FF701 does not inhibit HV. If no spontaneous systole appears, HV stimulates with the predetermined period X, and two consecutive stimulating impulses I are seen at the left of FIG. 23. A spontaneous systole SS may then take place. It comes in through D701 and is directed over 702 to discharge the capacitance HV through the discharge resistance. The waiting period begins. At the same time D701 now validates 703 and closes 702 for any consecutive spontaneous systole which may occur. At the same time that a pulse is transmitted through 702, D702 has directed the pulse from 701 to 705 and FF702 is then switched and the inhibition of HV' ceases. The capacitance of HV' begins to discharge. When no second spontaneous systole appears at the end of the discharge, HV stimulates by transmitting a stimulating pulse. This stimulating pulse I which appears on 721 before passing over 11, reswitches by means of 723, FF702 into the position in which it inhibits HV'. At the same time, through a line not shown, from 721, the pulse I delivered by HV returns D701 and 702 to their initial positions so that the directing means are again open towards 702 and 705. HV then continues to stimulate with a period X, again as seen on FIG. 23. A new spontaneous systole SS appears which acts like the one which has already been described, that is to say, it discharges the capacitance of HV through the discharge resistor and charges HV'. When a second spontaneous systole SS now takes place before the end of the waiting period HV, this second spontaneous systole now passes through 703, on the one hand, and 704 on the other hand. When passing through 703 it provokes the discharge of HV' through the discharge resistance of HV' thus initiating a new waiting period. At the same time, through the conductor 713, the pulse acts briefly on 1700 and rapidly discharges the capacitance of HV which immediately begins to recharge. The pulse which also passes through 704 has no effect, because FF701 is already swung into a position in which it does not inhibit HV. If no third spontaneous systole takes place, the end of the discharge of HV' causes a stimulation I as seen on FIG. 23. At the same time, D701 and D702 return to the open position, opening the path to 703 and 704 because they were changed in state during the occurrence of the second systole SS. It is now HV' which continues the stimulation at the predetermined period I. Be it supposed that after such a stimulation (right hand side of FIG. 23) a new spontaneous systole SS is produced. At this moment it passes through 703 and HV' discharges through its discharge resistance. A new spontaneous systole SS occurs after the end of this discharge, and the corresponding pulse will pass now through 702 and it is HV which had already been charged, which now must discharge into the discharge resistor, whereas HV' discharges abruptly under the influence of the pulse which arrives over 712 at the inhibitor I'700. Immediately HV' begins to recharge. A third spontaneous systole SS takes place before the end of the discharge of HV, and it is then HV which is abruptly discharged by the pulse passing through 713 whereas the pulse passing through 703 discharges HV' through its discharge resistance until stimulation I is produced.

It will be understood that in this manner, by regulating Y to be constantly less than K, tachycardia is efficaciously combated.

It goes without saying that the device of FIG. 22 may be made in many other ways. In particular, instead of utilizing condensers in the devices such as HV, the man skilled in the art could, without resorting to invention, produced a digitally operating device carrying out the various functions according to the invention, the technique of transformation into digital operation being well known as shown in particular by the digital device described on FIG. 16.

What is claimed is:

1. A method of electrically stimulating the cardiac muscle by means of an automatic device comprising heart stimulating and detecting means, which method comprises the steps of:
    A. detecting heart signals including spontaneous heart signals,
    B. transmitting electrical stimulating pulses to the cardiac muscle at a predetermined frequency in the absence of a spontaneous heart signal,
    C. suspending the transmission of an electrical stimulating pulse for a waiting period when a spontaneous signal is detected,
    D. detecting among said detected spontaneous heart signals, those which are dangerous,
    E. counting said dangerous heart signals,
    F. and, if a predetermined number of said dangerous heart signals is counted during occurrence of a total predetermined number of said detected heart signals, transmitting electrical stimulating pulses to the cardiac muscle with temporarily increased frequency.

2. A method as claimed in claim 1 wherein said predetermined number and said total predetermined number are equal in order to stimulate the cardiac muscle with said increased frequency when the counted number of directly consecutive dangerous signals reaches said predetermined number.

3. A method as claimed in claim 2 wherein said predetermined number is comprised between 2 and 12.

4. A method as claimed in claim 1, wherein said predetermined number is less than said total predetermined number, and said total predetermined number is comprised between 2 and 12.

5. A method as claimed in claim 1 comprising the step of sensing the time between a detected spontaneous heart signal and an immediately preceding detected heart signal and counting said spontaneous heart signal as a dangerous one if said sensed time is greater than the refractory period of the cardiac muscle and less than a fixed interval which is less than the time period corresponding to said predetermined frequency.

6. In an automatic device for electrically stimulating the cardiac muscle, comprising heart stimulating and detecting means, means for transmitting electrical stimulating pulses to the cardiac muscle at a predetermined frequency in the absence of a spontaneous heart signal and means for suspending the transmission of an electrical stimulating pulse for a waiting period when a spontaneous signal is detected, the improvement which comprises first counting means for periodically counting a predetermined total number of detected heart signals, second counting means for simultaneously counting the detected dangerous heart signals and means responsive thereto for temporarily stimulating the cardiac muscle at an increased frequency when the number of counted dangerous heart signals reaches a predetermined number less than or equal to said total predetermined number.

7. A device as claimed in claim 6 comprising gate means connected to said detecting means, means responsive to said detection means to open said gate means after a fixed time period following a heart signal detection and greater than the refractory period of the cardiac muscle and to close said gate means after a fixed time interval being less than the period corresponding to said predetermined frequency, said second counting means being responsive to said gate means when opened.

8. A device as claimed in claim 6, wherein, when said second counting means have counted said predetermined number of dangerous signals, a pulse is transmitted to a flip-flop to switch said flip-flop, said flip-flop being connected to said first counting means to reset said first counting means to zero when switched and being also connected to said means for temporarily increasing said frequency.

9. A device as claimed in claim 8, wherein said means for temporarily increasing said frequency comprise a time base for generating stimulating pulses at increased frequency and further means actuated by said flip-flop or temporarily authorizing operation of said time base, said further means being also connected to said flip-flop to switch back said flip-flop at the end of authorization, said further means being also connected to said second counting means to reset said second counting means to zero at the end of said authorization.

10. A method of electrically stimulating the cardiac muscle by means of an automatic device comprising heart stimulating and detecting means, which method comprises the steps of:
    A. detecting and counting heart signals including spontaneous heart signals, B. transmitting electrical stimulating pulses to the cardiac muscle at a predetermined frequency in the absence of a spontaneous heart signal,
C. suspending the transmission of an electrical stimulating pulse for a waiting period when a spontaneous signal is detected,
D. detecting among said detected spontaneous heart signals, those which are dangerous,
E. counting said dangerous heart signals,
F. and, if the proportion of said dangerous heart signals relative to the total number of said detected heart signals is greater than a predetermined value, transmitting electrical stimulating pulses to the cardiac muscle with temporarily increased frequency.

* * * * *